US007700557B2

(12) United States Patent
Backer et al.

(10) Patent No.: US 7,700,557 B2
(45) Date of Patent: Apr. 20, 2010

(54) RECOMBINANT PROTEINS CONTAINING SHIGA-LIKE TOXIN AND VASCULAR ENDOTHELIAL GROWTH FACTOR FRAGMENTS

(75) Inventors: Marina V. Backer, Simsbury, CT (US); Joseph M. Backer, Simsbury, CT (US)

(73) Assignee: SibTech, Inc., Brookfield, CT (US)

( * ) Notice: Subject to any disclaimer, the term of this patent is extended or adjusted under 35 U.S.C. 154(b) by 203 days.

(21) Appl. No.: 11/891,863

(22) Filed: Aug. 14, 2007

(65) Prior Publication Data

US 2009/0023649 A1 Jan. 22, 2009

Related U.S. Application Data

(60) Division of application No. 10/765,580, filed on Jan. 27, 2004, now Pat. No. 7,267,973, which is a continuation-in-part of application No. 09/796,861, filed on Mar. 1, 2001, now abandoned.

(60) Provisional application No. 60/190,973, filed on Mar. 22, 2000.

(51) Int. Cl.
*A61K 38/18* (2006.01)
*C07K 14/475* (2006.01)
(52) U.S. Cl. .......................... 514/12; 530/399; 530/402
(58) Field of Classification Search ........................ None
See application file for complete search history.

(56) References Cited

U.S. PATENT DOCUMENTS

| 6,036,955 A | 3/2000 | Thorpe et al. ............. 424/136.1 |
| 6,037,329 A | 3/2000 | Baird et al. .................... 514/44 |

OTHER PUBLICATIONS

Aiello et al., "Hypoxic Regulation of Vascular Endothelial Growth Factor in Retinal Cells", *Arch/Ophthalmol.*, vol. 113, pp. 1538-1544, 1995.
Al-Jaufy et al., Cytotoxicity of a Shiga Toxin A Subunit-CD4 Fusion Protein to Human Imunodeficiency Virus-Infected Cells, *Infection and Immunity*, vol. 62, No. 3, pp. 956-960, 1994.
Al-Jaufy et al., "Purification and Characterization of a Shiga Toxin A Subunit-CD4 Fusion Protein Cytotoxic to Hummam Immunodeficiency Virus-Infected Cells", *Infection and Immunity*, vol. 63, No. 8, pp. 3073-3078, 1995.
Arora et al., "Vascular Endothelial Growth Factor Chimeric Toxin Is Highly Active against Endothelial Cells", *Cancer Research*, vol. 59, pp. 183-188, 1999.
Takayuki et al., "Molecular and Cellular Cardiology/Gene Transfer: Accelerated Restitution of Endothelial Integrity and Endothelium-Dependent Function After pvVEGF sub 165 Gene Transfer", *Ovid: Ashara: Circulation*, vol. 94 (12), pp. 3291-3302, 1996.
Bikfalvi et al., "Interaction of Vasculotropin/Vascular Endothelial Cell Growth Factor With Human Umbilical Vein Endothelial Cells: Binding, Internalization, Degradation, and Biological Effects", *Journal of Cellular Physiology*, vol. 149, pp. 50-59, 1991.

Brown et al., "Increased Expression of Vascular Permeability Factor (Vascular Endothelial Growth Factor) and Its Receptors in Kidney and Bladder Carcinomas", *American Journal of Pathology*, vol. 143, No. 5, pp. 1255-1262, 1993.
Brown et al., "Expression of Vascular Permeability Factor (Vascular Endothelial Growth Factor) and Its Receptors in Breast Cancer", *Human Pathology*, vol. 26, pp. 86-91, No. 1, 1995.
Cao et al., "Construction of Mutant Genes for a Non-Toxic Verotoxin 2 Variant (VT2vp1) of *Escherichia coli* and Characterization of Purified Mutant Toxins", *Microbiol. Immunol.*, 38(6), pp. 441-447, 1994.
Claffey et al., "Regulation of VEGF/VPF expression in tumor cells: Consequences for tumor growth and metastasis", *Cancer and Metastasis Review*, 15, pp. 165-176, 1996.
Couffinhal et al., "Vascular Endothelial Growth Factor/Vascular Permeability Factor (VEGF/VPF) in Normal and Atherosclerotic Human Arteries", *American Journal of Biology*, vol. 150, No. 5, pp. 1673-1685, 1997.
Deresiewicz et al., "The role of tyrosine-114 in the enzymatic activity of the Shiga-like toxin 1 A-chain", *Mol. Gen. Genet*, vol. 241, pp. 467-473, 1993.
Detmar et al., "Overexpression of Vascular Permeability Factor/Vascular Endothelial Growth Factor and its Receptors in Psoriasis", *J. Exp. Med.*, vol. 180, pp. 1141-1146, 1994.
Folkman et al., "Angiogenesis", *The Journal of Biological Chemistry*, vol. 267, No. 16, pp. 10931-10934, 1992.
Folkman, "Angiogenesis in cancer, vascular, rheumatoid and other disease", *Nature Medicine*, vol. 1, pp. 27-31, 1995.
Haddad et al., "Minimum Domain of the Shiga Toxin A Subunit Required for Enzymatic Activity", *Journal of Bacteriology*, vol. 175, No. 16, pp. 4970-4978, 1993.
Hanahan, "Signaling Vascular Morphogenesis and Maintenance", *Science*, vol. 277(5322), pp. 48-50, 1997.
Jordanov et al., "Ribotoxic Street Response: Activation of the Stress-Activated Protein Kinase NK1 by Inhibitors of the Peptidyl Transferase Reaction and by Sequence-Specific RNA Damage to the α-Sarcin/Ricin Loop in the 28S rRNa", *Molecular and Cellular Biology*, vol. 17, No. 6, pp. 3373-3381, 1997.
Kaplan et al., "Recent advances in understanding the pathogenesis of the hemolytic uremic syndromes", *Pediatric Nephrology*, vol. 4, pp. 276-283, 1990.
Kim et al., "Inhibition of vascular endothelial growth factor-induced angiogenesis suppresses tumour growth in vivo", *Nature*, vol. 362, pp. 841-844, 1993.
Millauer et al., "Giloblastoma growth inhibited in vivo by a dominant-negative Flk-1 mutant", *Nature*, vol. 367, pp. 576-579, 1994.
Neufeld et al., "Vascular Endothelial Growth Factor And Its Receptors", *Progress in Growth Factor Research*, vol. 5, pp. 89-97, 1994.
Neufeld et al., "Vascular endothelial growth factor (VEGF) and its receptors", *The FASEB Journal*, vol. 13, pp. 9-22, 1999.

(Continued)

*Primary Examiner*—Robert C Hayes
(74) *Attorney, Agent, or Firm*—Todd E. Garabedian; Wiggin and Dana LLP

(57) ABSTRACT

The present invention is directed to an isolated polypeptide including: (1) the A subunit of Shiga-like bacterial toxin, wherein said subunit has the nucleic acid sequence of SEQ ID NO:9; and (2) human vascular endothelial growth factor wherein the growth factor has the nucleic acid sequence of SEQ ID NO:10; wherein the isolated polypeptide possesses ribosome inactivating activity. The present invention is also directed to compositions for inhibiting endothelial cell growth in a patient.

8 Claims, 8 Drawing Sheets

OTHER PUBLICATIONS

Olson et al., "Targeting The Tumor Vasculature: Inhibition Of Tumor Growth By A Vascular Endothelial Growth Factor-Toxin Conjugate", *Int. J. Cancer*, vol. 73, pp. 865-870, 1997.

Obrig et al., "Endothelial Heterogeneity in Shiga Toxin Receptors and Responses", *The Journal of Biological Chemistry*, vol. 268, No. 21, pp. 15484-15488, 1993.

Obrig et al., "Pathogenesis of Haemolytic Uraemic Syndrome", *The Lancet*, p. 687, Sep. 1987.

Plate et al., "Up-Regulation of Vascular Endothelial Growth Factor and Its Cognate Receptors in a Rat Glioma Model of Tumor Angiogenesis", *Cancer Research*, vol. 53, pp. 5822-5827, 1993.

Ramakrishnan et al., "Vascular Endothelial Growth Factor-Toxin Conjugate Specifically Inhibits *KDR/flk-1*-positive Endothelial Cell Proliferation in Vitro and Angiogenesis in Vivo", *Cancer Research*, vol. 56, pp. 1324-1330, 1996.

Richardson et al., "The Histopathology of the Hemolytic Uremic Syndrome Associated with Verocytotoxin-Producing *Escherichia coli* infections", *Human Pathology*, vol. 19, No. 9, pp. 1103-1108, 1988.

Saleh et al., "Inhibition of Growth of C6 Glioma Cells in Vivo by Expression of Antisense Vascular Endothelial Growth Factor Sequence", *Cancer Research*, vol. 56, pp. 393-401, 1996.

Saxena et al., "Shiga Toxin, Shig-like Toxin II Variant, and Ricin Are All Single-site RNA $N$-Glycosidases of 28 S RNA When Microinjected into *Xenopus* Oocytes", *The Journal of Biological Chemistry*, vol. 264, No. 1, pp. 596-601, 1989.

Terman et al., "Biological properties of VEGF/VPF receptors", *Cancer and Metastasis Reviews*, vol. 15, pp. 159-163, 1996.

Vallera et al., "Renal dysfunction accounts for the dose limiting toxicity of $DT_{390}$ati-CD#sFv, a potential new recombinant anti-GVHD immunotixin", *Protein Engineering*, vol. 10, No. 9, pp. 1071-1076, 1997.

Veikkola et al., "VEGFs, receptors and angiogenesis", *Cancer Biology*, vol. 9, pp. 211-220, 1999.

Brigotti et al., "The RNA-$N$-Glycosidase Activity of Shiga-Like Toxin I: Kinetic Parameters of the Native and Activated Toxin", *Toxicom*, vol. 35, No. 9, pp. 1431-1437, 1997.

M. V. Backer, et al., "Engineering S-protein fragments of bovine ribonuclease A for targeted drug delivery", *National Library of Medicine*, vol. 26, No. 3, pp. 455-461, 2002.

M. V. Backer, et al., "Targeting endothelial cells overexpressing VEGFR-2: selective toxicity of Shiga-like toxin-VEGF fusion proteins", *National Library of Medicine*, vol. 12, No. 6, pp. 1066-1073, 2001.

M. V. Backer, et al., "Shiga-like toxin-VEGF fusion proteins are selectively cytotoxic to endothelial cells overexpressing VEGFR-2," *National Library of Medicine*, vol. 74, No. 1-3, pp. 349-355, 2001.

FIG.1

RECOMBINANT PROTEINS CONTAINING SHIGA-LIKE TOXIN AND VASCULAR ENDOTHELIAL GROWTH FACTOR FRAGMENTS

This Application is a Divisional Application of U.S. Ser. No. 10/765,580 filed Jan. 27, 2004 now U.S. Pat. No. 7,267, 973, which is a Continuation-in-Part Application of U.S. Ser. No. 09/796,861 filed Mar. 1, 2001 now abandoned, which claims the benefit of U.S. Provisional Application Ser. No. 60/190,973 filed Mar. 22, 2000. These applications are herein incorporated by reference in their entireties.

STATEMENT OF GOVERNMENT SUPPORT

This invention was made in part with government support under grant number 1R43CA81832-01 from the National Institutes of Health. The government has certain rights in this invention.

BACKGROUND OF THE INVENTION

1. Field of the Invention

The present invention relates to recombinant nucleic acid molecules and recombinant fusion proteins, and more particularly to Shiga-like toxin-vascular endothelial growth factor fusion proteins and recombinant DNA molecules coding for such fusion proteins. The present invention also relates to bacterial vectors containing the above recombinant nucleic acid molecules, methods of producing the above fusion proteins, and their use in therapeutic treatments.

2. Description of the Related Art

Angiogenesis is a tightly controlled process of growing new blood vessels (see, Folkman & Shing, 1992; Hanahan, 1997, for reviews). Under normal circumstances angiogenesis occurs only during embryonic development, wound healing and development of the corpus luteum. However, angiogenesis occurs in a large number of pathologies, such as solid tumor and metastasis growth, various eye diseases, chronic inflammatory states, and ischemic injuries (see, Folkman, 1995, for review). Thus, growing endothelial cells present unique targets for treatment of several major pathologies.

The crucial positive regulator of angiogenesis is vascular endothelial growth factor (VEGF) also known as vascular permeability factor (see, Neufeld, et al, 1999 for reviews). VEGF is a secreted dimeric glycoprotein that, as a result of alternative splicing, may consist of polypeptides with 121, 145, 165, 189 and 206 amino acid residues. VEGF is expressed by normal and tumor cells and the control of VEGF expression appears to be regulated on several levels (see, Claffey & Robinson, 1996, Veikkola & Alitalo, 2000, for reviews). Expression of VEGF is upregulated in response to hypoxia and nutritional deprivation suggesting a feedback loop between tumor and metastasis growth and the ability of tumor cells to induce host angiogenic responses.

The action of VEGF on endothelial cells is mediated by tyrosine kinase flt-1 and KDR/flk-1 receptors, also known as VEGFR-1 and VEGFR-2 (see, Terman, & Dougher-Vermazen, 1996; Veikkola, et al, 2000, for review). These receptors are preferentially expressed on endothelial cells. There are reports that endothelial cells at the sites of angiogenesis express significantly higher numbers of KDR/Flk1 receptors than quiescent endothelial cells (Brown, et al., 1993, 1995; Plate, et al., 1993; Detmar, et al., 1994; Couffinhal, et al., 1997). The receptors are single span transmembrane protein tyrosine kinase that belong to the immunoglobulin superfamily and contains seven Ig-like loops in the extracellular domain and shares homology with the receptor for platelet-derived growth factor. VEGF binding to these receptors induces receptor dimerization followed by tyrosine phosphorylation of the SH2 and SH3 domains in the dimer (see, Neufeld, et al., 1994 for review). KDR/Flk1-VEGF complex is internalized via receptor-mediated endocytosis (Bikfalvi, et al., 1991).

Several groups reported that targeting of either VEGF or KDR/flk-1 inhibits angiogenesis and angiogenesis-dependent processes (Kim, et al., 1993; Millauer, et al., 1994; Saleh, et al., 1996; Aiello, et al., 1995). On the other hand, direct injection of VEGF or a plasmid encoding VEGF into ischemic tissues in a model system promoted development of microvasculature and improved recovery after ischemic injury or balloon angioplasty (Asahara, et al., 1996). Taken together, these results leave little doubt that VEGF and KDR/Flt1 play crucial roles in angiogenesis. Although these experiments provided a "proof-of-principle" that VEGF-toxin conjugates or fusion proteins may work in vivo, further development of DT-VEGF constructs is doubtful, because of the renal and liver toxicity of DT-containing fusion proteins (see, for example, Vallera et al., 1997).

Since VEGF binds specifically to endothelial cells, this growth factor provides a unique opportunity for targeted drug delivery to the sites of angiogenesis. It was demonstrated that catalytically active forms of diptheria toxin covalently linked or fused via recombinant DNA technology to recombinant VEGF165 and/or VEGF121 are selectively toxic against cells expressing KDR/flk-1 receptors and also suppressed angiogenesis in vivo (Ramakrishnan, et al., 1996; Olson et al., 1997; Arora, et al., 1999).

It is advantageous to use VEGF for targeting toxins that are "natural killers" of endothelial cells. Shiga-like toxin 1 produced by $E.$ $coli$ O157:H7 is such a "natural killer" for endothelial cells. Damage to endothelial cells caused by Shiga-like toxins 1 plays a causative role in the pathogenesis of hemorrhagic colitis (HC) and hemolytic uremic syndrome (HUS) induced by $E.$ $coli$ O157:H7 (Obrig, et al., 1987, 1993; Richardson, et al., 1988; Kaplan, et al., 1990).

Shiga-like toxin 1 (SLT-1) is composed of a single copy of a 32 kDa A-subunit associated with a ring shaped pentamer of receptor-binding 7 kDa B-subunits. B-subunits bind SLTs to the cellular receptor globotrioaosylceramide known as $Gb_3$ (Obrig et al., 1993). This receptor is found on many cell types including endothelial cells (Obrig et al., 1993). After binding to the cell surface receptor, SLT is endocytosed and A-subunit is cleaved into $A_1$ (27.5 kDa) and $A_2$ (4.5 kDa) forms that are linked by disulphide bond (Olsnes et al., 1981). Processed A subunit is a specific N-glycosidase that inactivates ribosomes by cleaving off a single adenine residue in the position 4324 from 5' terminus of 28S rRNA of 60S ribosome subunit (Saxena et al., 1989). The cleavage of $A_{4324}$ from 28S rRNA inactivates ribosomes by inhibiting binding of the elongation factor (EF-1)/aminocyl-tRNA complex to ribosomes, resulting in the inhibition of the protein synthesis. As with other ribosome-inactivating agents, the subsequent cytostatic and cytotoxic effects might arise as a cellular response to inactivation of a relatively small proportion of ribosomes through ribotoxic stress response (Iordanov et al., 1997). Alternatively, cytostatic and cytotoxic effects might arise as a cellular response to a massive collapse of protein synthesis due to inactivation of a large number of ribosomes. It is important that the unprocessed, full length A subunit as well as various truncated A subunits retain significant N-glycosidase activity (Haddad, et al., 1993; Al-Jaufy, et al., 1994, 1995). Furthermore, fusion proteins containing unprocessed, full length A subunit as well as various truncated A subunits fused to N-terminus of CD4 retain N-glycosidase activity and are cytotoxic for cells expressing HIV-1 gp120-gp41 complex (Al-Jaufy, et al., 1994, 1995).

Since Shiga-like toxin is a "natural" killer of endothelial cells it is advantageous to deliver enzymatically active full-length, truncated or mutated A subunit into endothelial cells in order to inhibit their growth and/or kill them. To avoid damage to other cell type the enzymatically active full-length, truncated or mutated A subunit should be delivered into target cells by endothelial cell specific growth factor such as VEGF. Therefore, it is an object herein to provide effective recombinant DNA methods for the production of fusion proteins containing enzymatically active full-length, truncated or mutated A subunit fused to full-length, truncated or mutated VEGF that retain ability to bind to VEGF receptors.

SUMMARY OF THE INVENTION

In one aspect, the present invention is directed to an isolated nucleic acid encoding a fusion protein comprising: (1) the A subunit of Shiga-like bacterial toxin, or a truncated or mutated version thereof; and (2) human vascular endothelial growth factor, or a truncated or mutated version thereof; wherein the fusion protein possesses ribosome inactivating activity.

In another aspect, the present invention is directed to an isolated polypeptide comprising: (1) the A subunit of Shiga-like bacterial toxin, or a truncated or mutated version thereof; and (2) human vascular endothelial growth factor, or a truncated or mutated version thereof; wherein the isolated polypeptide possesses ribosome inactivating activity.

In another aspect, the present invention is directed to an expression vector, comprising: (1) a nucleic acid encoding a fusion protein comprising the A subunit of Shiga-like bacterial toxin, or a truncated or mutated version thereof; and human vascular endothelial growth factor, or a truncated or mutated version thereof; and (2) a promoter sequence operably linked to the nucleic acid to allow expression of the nucleic acid.

In another aspect, the present invention is directed to a bacterial cell transformed with the above expression vector.

In yet another aspect, the present invention is directed to a method of inactivating ribosomes in a cell, comprising the steps of: (a) contacting a cell with a polypeptide comprising: (1) the A subunit of Shiga-like bacterial toxin, or a truncated or mutated version thereof; and (2) human vascular endothelial growth factor, or a truncated or mutated version thereof; under conditions which permit the polypeptide to be internalized into the cell and inactivate ribosomes in the cell.

In yet another aspect, the present invention is directed to a composition for inhibiting endothelial cell growth in a patient, comprising: (A) a fusion protein comprising the A subunit of Shiga-like bacterial toxin, or a truncated or mutated version thereof; and human vascular endothelial growth factor, or a truncated or mutated version thereof, the fusion protein possessing ribosome inactivating activity; and (B) a pharmaceutically acceptable carrier.

In yet another aspect, the present invention is directed to a method of treating a patient suffering from a pathophysiological condition that depends on angiogenesis, comprising: providing to the patient an effective amount of a composition comprising a fusion protein comprising the A subunit of Shiga-like bacterial toxin, or a truncated or mutated version thereof; and human vascular endothelial growth factor, or a truncated or mutated version thereof, the fusion protein possessing ribosome inactivating activity; and a pharmaceutically acceptable carrier.

In addition, the proteins and pharmaceutical compositions of the present invention may be used either alone, or in combination with other treatments for diseases related to angiogenesis, particularly treatments whose efficacy is enhanced by decrease in oxygen or nutrient supplies that would arise from damage to endothelium caused by said protein and pharmaceutical compositions.

These and other aspects will be described in more details in the following detailed description of the invention.

BRIEF DESCRIPTION OF THE FIGURES

The invention will be more fully understood from the following detailed description taken in conjunction with the accompanying figures in which:

FIG. 1 is a schematic representation of SLT-VEGF/L, catalytically inactive SLT-VEGF/Lci, and SLT-VEGF/S proteins. Catalytically inactive SLT-VEGF/Lci was constructed in order to separate the effects of ribosome inactivation from other effects that might be induced by recombinant SLT-VEGF proteins. This protein contains a double mutant A-subunit with Y114S and R170L amino acid substitutions that independently significantly decrease the enzymatic activity of SLT-1 A-subunit, while not affecting its folding as judged by unchanged antigenic properties (Deresiewicz et al., 1993; Cao et al., 1994). His- and S-tag are used for purification and quantitation. Cleavage site for intracellular protease furin that cleaves A subunits into disulphide bond linked A1-A2 dimers is indicated. Recombinant VEGF121 protein used in control experiments also contains His- and S-tags.

FIG. 2 also illustrates the quality of final preparations of VEGF121 (lane V), SLT-VEGF/L, SLT-VEGF/Lci, and SLT-VEGF/S proteins obtained after purification from Origami (DE3) pLysS E. coli strain (FIG. 2, panel C). Expression of SLT-VEGF fusion proteins was induced by addition of isopropyl-β-D-thio-galactopyronoside (IPTG). BL21 (DE3) pLysS cells were harvested after 3.5 hours IPTG induction for SLT-VEGF/L and after 2 hours of IPTG induction for SLT-VEGF/S at 37° C. Origami (DE3) pLysS cells were harvested after 4 hours IPTG induction for both proteins at 30° C. Soluble fractions (S), inclusion bodies (I), and refolded proteins purified from inclusion bodies were analyzed by SDS-PAGE on 15% gels. Molecular weights of markers in lane M are indicated in kDa.

Figure 5A:
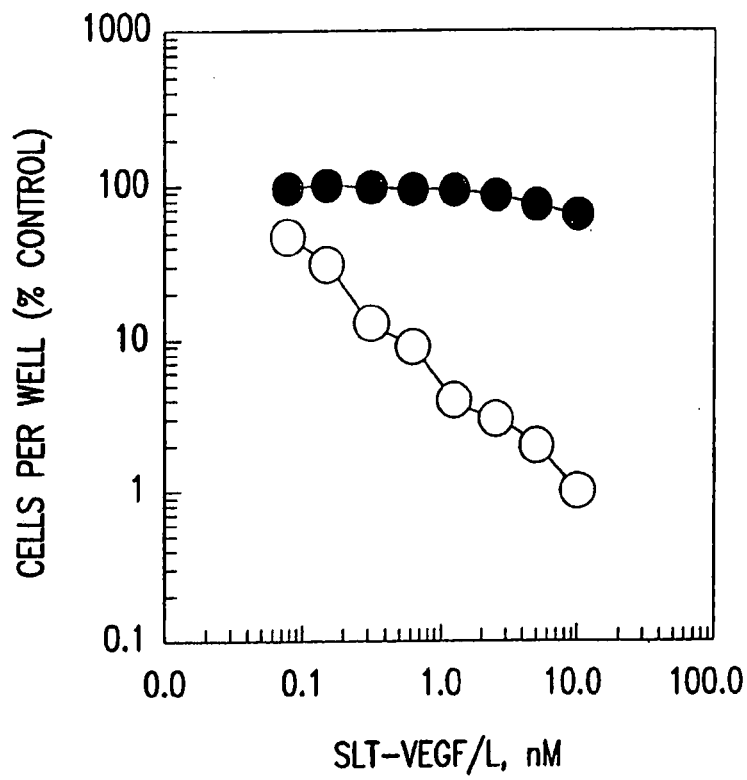
Figure 5B:
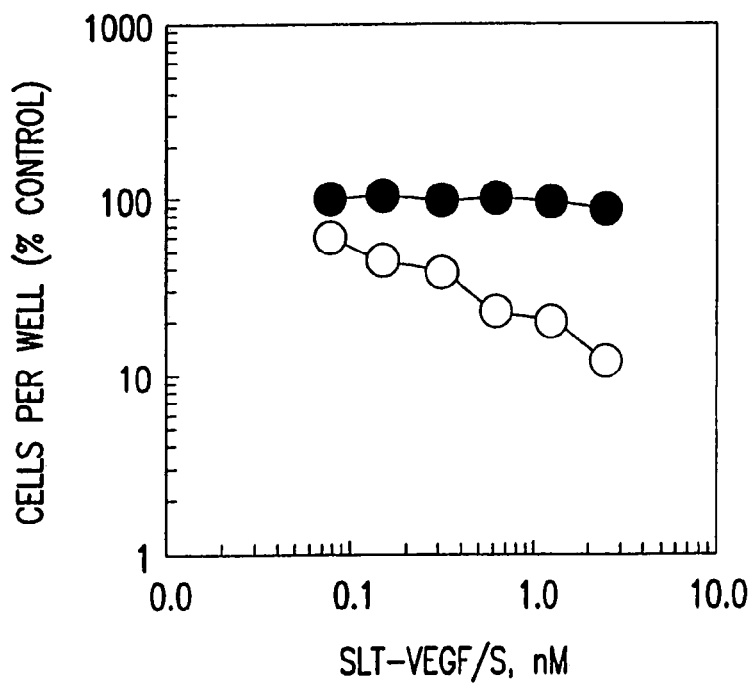
Figure 5C:
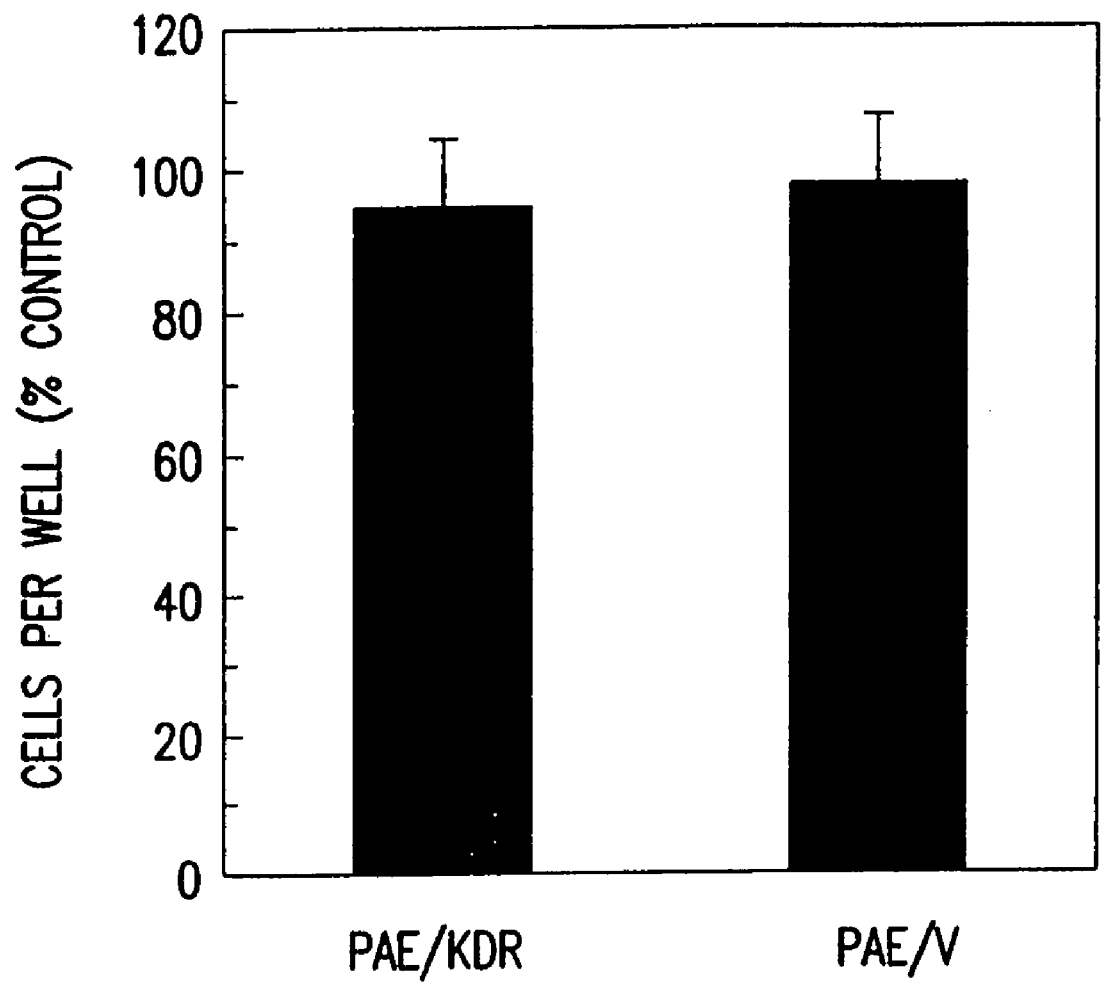

FIG. 5 illustrates that SLT-VEGF/L and SLT-VEGF/S proteins target growing PAE/KDR cells that overexpress KDR/flk-1 receptors (open circles) but do not affect control PAE/V cells that do not express KDR/flk-1 receptors (filled circles). PAE/KDR cells and control PAE/V cells lacking KDR/flk-1 receptors were plated at ~5,000 cells/well and treated for 72 hours with SLT-VEGF/L (FIG. 5, panel A) or SLT-VEGF/S (FIG. 5, panel B) isolated from Origami (DE3) lysS host. As shown in FIG. 5, SLT-VEGF proteins strongly inhibit growth of PAE/KDR cells overexpressing KDR/flk-1 receptors. This effect is thought to be due to the ribosome-inactivating activity of SLT moiety, because catalytically inactive SLT-VEGF/Lci protein does not affect growth of PAE/KDR and PAE/V cells (FIG. 5, panel C).

Figure 6A:
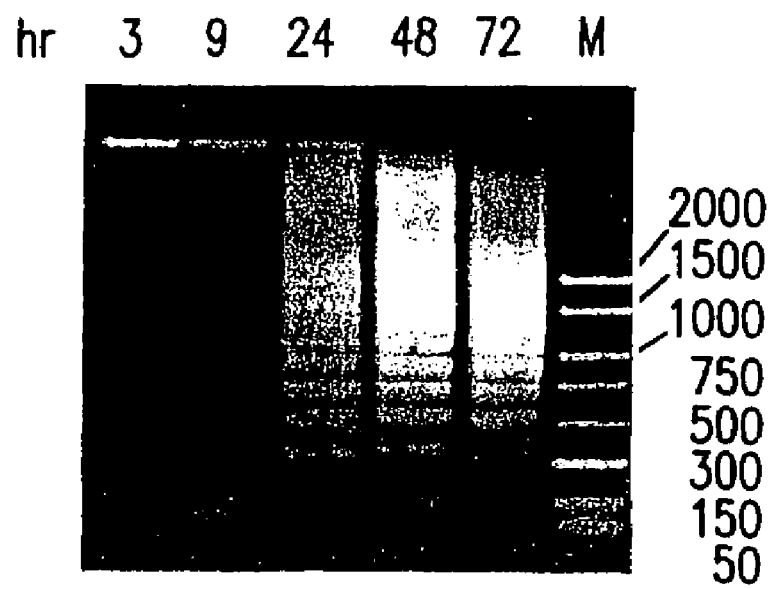
Figure 6B:
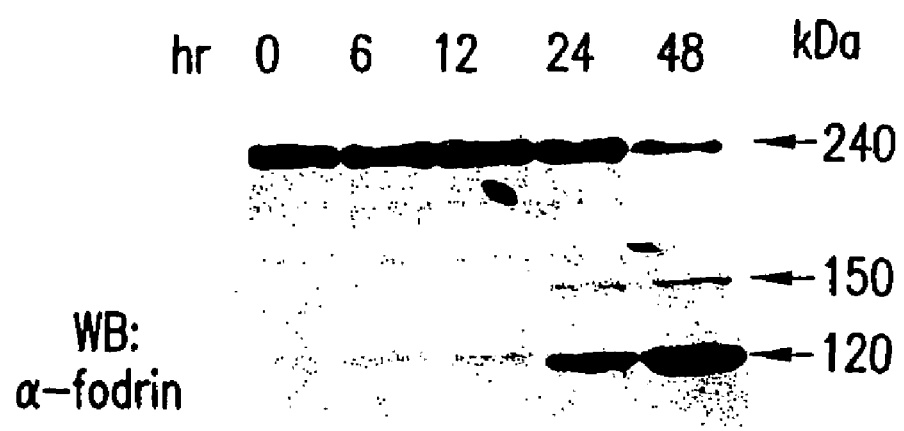

FIG. 6 illustrates that SLT-VEGF/L fusion protein rapidly activates apoptosis in PAE/KDR cells as judged by DNA degradation (FIG. 6, panel A) and cleavage of α-fodrin (FIG. 6, panel B).

Figure 7A:
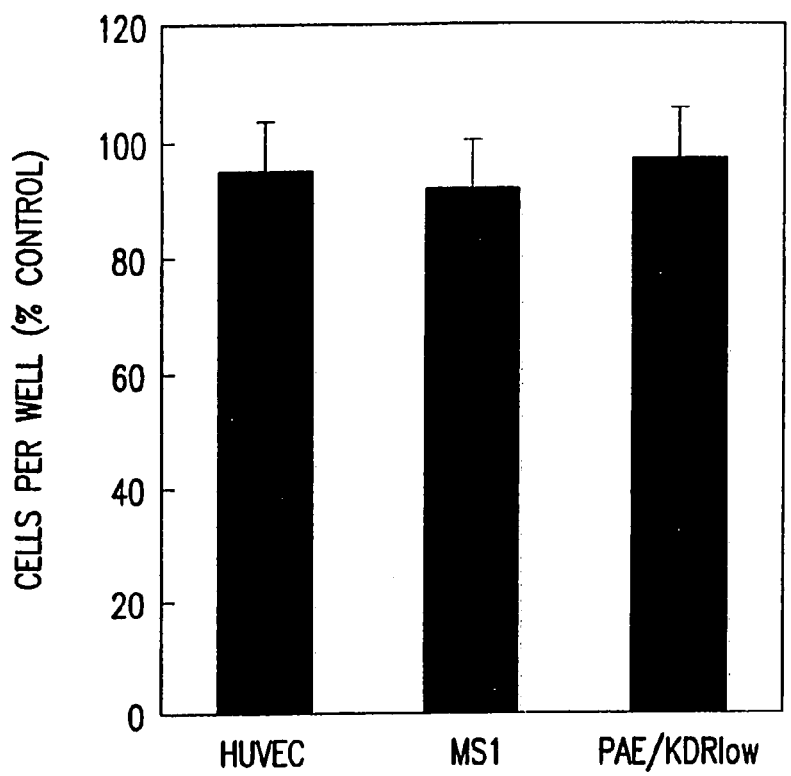
Figure 7B:
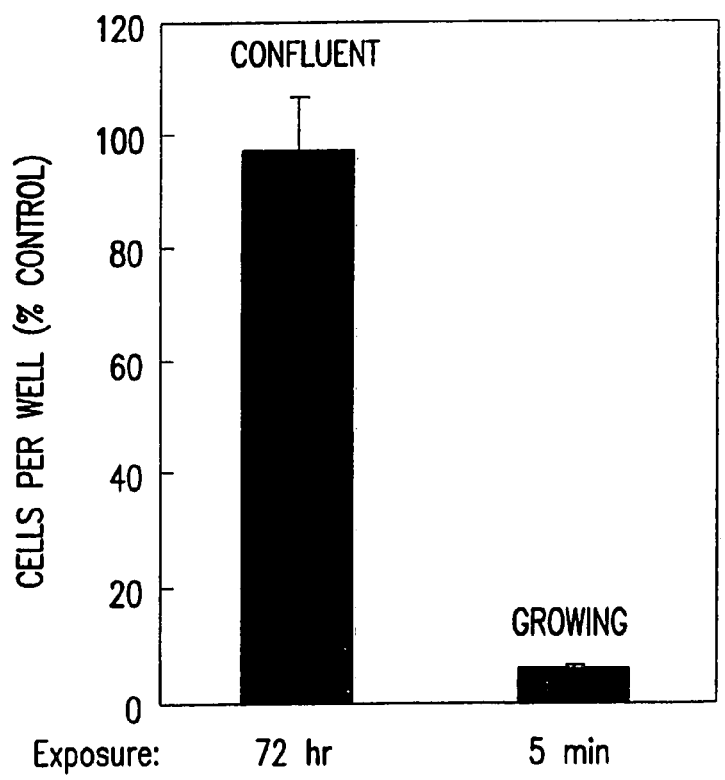

FIG. 7 illustrates that SLT-VEGF/L proteins do not target endothelial cells with a low number of KDR/flk-1 receptors (FIG. 7, panel A) and quiescent PAE/KDR cells (FIG. 7, panel B). As estimated by Western blot analysis, human umbilical vein endothelial (HUVE) cells express 30,000-50,000 KDR/flk-1 receptors per cell, and PAE/KDR$_{low}$ cells express ~5,000 KDR/flk-1 receptors per cell. MS1 cells expressed ~20,000 VEGFR-2/cells. HUVE, PAE/KDR$_{low}$, and MS1 cells were plated onto 24-well plates at densities of 5–10×10$^3$ cells/well and exposed to 2.5 nM SLT-VEGF/L 20 hr later and counted after 72 hrs. Confluent PAE/KDR were maintained at confluence for 3 days, then treated with 20 nM SLT-VEGF/L for 72 hrs. Growing PAE/KDR were exposed to 20 nM SLT-VEGF/L for 5 min; then shifted to fresh culture medium and counted after 72 hrs.

DETAILED DESCRIPTION OF THE INVENTION

An object of the present invention is to provide nucleic acid sequences, such as DNA or RNA sequences that code for fusion proteins herein named SLT-VEGF. The SLT-VEGF fusion proteins include a full-length, truncated, or mutated A subunit of Shiga-like bacterial toxin which confers ribosome inactivating activity, and a vascular endothelial growth factor (VEGF) that binds to VEGF receptors. The three nucleic acid sequences and resulting protein sequences are preferably separated by a spacer sequence.

The nucleic acid sequences for the Shiga-like toxin and the VEGF are individually known in the art. However, the inventors have surprisingly found that a combination of these two sequences provides for production of a fusion protein with a unique combination of characteristics. The fusion protein is capable of binding to specific VEGF cellular receptor by virtue of the VEGF domain. The fusion protein is also capable of inactivating ribosomes and inducing apoptosis in endothelial cells overexpressing KDR/flk-1 receptors by virtue of the Shiga-like toxin domain. In combination, these two protein domains provide an effective and highly targeted treatment for diseases relating to angiogenesis.

Still another object of the invention is to provide a pharmaceutical composition for use in inhibition of endothelial cell growth, and containing the SLT-VEGF fusion proteins and a pharmaceutically acceptable carrier. Useful carriers include water, buffered saline, or other pharmaceutically acceptable carrier known in the art. The SLT-VEGF fusion proteins of the pharmaceutical composition are potent cytotoxic or cytostatic agents and are useful in treating of a variety of pathophysiological conditions that depend on angiogenesis, such as solid tumor and metastasis growth, various eye diseases, chronic inflammatory states, and ischemic injuries. In addition, the proteins and pharmaceutical compositions of the present invention may be used either alone, or in combination with other know treatments for diseases related to angiogenesis, particularly treatments whose efficacy is enhanced by decrease in oxygen or nutrient supplies that would arise from damage to endothelium caused by said protein and pharmaceutical compositions.

Yet another object of the invention is to provide recombinant expression vectors harboring the new DNA sequences and transformed bacterial cells containing such recombinant expression vectors. The nucleic acid sequences coding for the fusion protein SLT-VEGF may be inserted into known vectors, such as a bacterial plasmid or viral vector, using materials and methods well known in the art. The nucleic acid construct coding for the SLT-VEGF fusion proteins is inserted into a plasmid such that nucleic acid construct is operatively linked to an inducible promoter sequence, a sequence that encodes tags that simplify purification and quantitation of the fusion protein, and terminator functionality in the selected host. The plasmid is also preferably introduced into a host cell, such as a bacterial cell, in which the promoter is inducibly regulated.

Another object of the invention are methods for inhibiting growth of endothelial cells, and treating a patient suffering from a pathophysiological condition that depends on angiogenesis, such as solid tumor and metastasis growth, various eye diseases, chronic inflammatory states, and ischemic injuries.

In the fusion protein expressed by the recombinant nucleic acid sequence according to the present invention, the VEGF thereof is suitably selected from full-length or mutants of VEGF121, VEGF165, VEGF189 and VEGF209 capable of binding to high affinity receptors of VEGF. According to a particularly preferred embodiment of the invention, the VEGF is constituted by VEGF121 or truncated VEGF mutants thereof.

As used herein, Shiga-like toxin A subunit (abbreviated herein as SLT) refers to polypeptide having amino acid sequences found in *E. coli* O157:H7, as well as modified sequences, having amino acid substitutions, deletions, insertions or additions, which still express substantial ribosome inactivating activity. For some applications, such as various control experiments, it may be beneficial to produce SLT lacking ribosome inactivating activity. In particular, such modified SLTs may be produced by modifying the DNA disclosed herein by altering one or more amino acids or deleting or inserting one or more amino acids that may render it more suitable to achieve desired properties of SLT-VEGF fusion proteins. Such properties include but not limited to yield of recombinant protein in bacterial host, ability to bind to cellular VEGF receptor, ability to be internalized via receptor-mediated uptake, intracellular protein synthesis inhibitory activity, overall cytotoxic or cytostatic effects, pharmacokinetics and pharmacodynamics, and stability under various storage and use conditions. Any such protein, or version thereof, that, when fused to VEGF as described herein, that exhibits ribosome inactivating activity and ability to bind to cellular VEGF receptors in standard in vitro or in vivo assays is contemplated for use herein.

In one embodiment, Shiga-like toxin A subunit may be obtained from available nucleic acid sequences, such as the SLT A-subunit sequence found in GenBank (Accession No. AB015056), herein incorporated by reference. In a preferred embodiment, one SLT-1 A-subunit useful in the present invention is encoded by a nucleic acid sequence that comprises nucleotides 67-945 of the mature SLT-1 A-subunit available from GenBank (Accession No. AB015056). That sequence is as follows:

(SEQ ID NO:9)
AAGGAATTTACCTTAGACTTCTCGACTGCAAAGACGTATGTAGATTCGCT

GAATGTCATTCGCTCTGCAATAGGTACTCCATTACAGACTATTTCATCAG

GAGGTACGTCTTTACTGATGATTGATAGTGGCACAGGGGATAATTTGTTT

GCAGTTGATGTCAGAGGGATAGATCCAGAGGAAGGGCGGTTTAATAATCT

ACGGCTTATTGTTGAACGAAATAATTTATATGTGACAGGATTTGTTAACA

GGACAAATAATGTTTTTTATCGCTTTGCTGATTTTTCACATGTTACCTTT

CCAGGTACAACAGCGGTTACATTGTCTGGTGACAGTAGCTATACCACGTT

ACAGCGTGTTGCAGGGATCAGTCGTACGGGATGCAGATAAATCGCCATT

CGTTGACTACTTCTTATCTGGATTTAATGTCGCATAGTGGAACCTCACTG

ACGCAGTCTGTGGCAAGAGCGATGTTACGGTTTGTTACTGTGACAGCTGA

AGCTTTACGTTTTCGGCAAATACAGAGGGGATTTCGTACAACACTGGATG

ATCTCAGTGGGCGTTCTTATGTAATGACTGCTGAAGATGTTGATCTTACA

TTGAACTGGGGAAGGTTGAGTAGCGTCCTGCCTGACTATCATGGACAAGA

CTCTGTTCGTGTAGGAAGAATTTCTTTTGGAAGCATTAATGCAATTCTGG

GAAGCGTGGCATTAATACTGAATTGTCATCATCATGCATCGCGAGTTGCC

AGAATGGCATCTGATGAGTTTCCTTCTATGTGTCCGGCAGATGGAAGAGT

CCGTGGGATTACGCACAATAAAATATTGTGGGATTCATCCACTCTGGGGG

CAATTCTGATGCGCAGAACTATTAGCAGT

As used herein, SLT-VEGF proteins are fusion proteins containing an SLT polypeptide and vascular endothelial growth factor (VEGF), that is reactive with VEGF cell surface receptor.

The resulting SLT-VEGF fusion proteins are useful as cytotoxic or cytostatic agents that target and inhibit growth of endothelial cells and thereby are useful for treating angiogenesis-dependent diseases, including, but not limited to, solid tumor and metastasis growth, various eye diseases, chronic inflammatory states, and ischemic injuries.

As used herein, to target SLT-VEGF protein means to direct it to a cell that expresses VEGF receptors. Upon binding to the receptor SLT-VEGF protein is internalized by the cell and is cytotoxic or cytostatic to the cell.

As used herein, the term active, or reference to the activity of SLT-VEGF proteins or cytotoxic and cytostatic effects of SLT-VEGF proteins, refers to the ability of such proteins to inactivate ribosomes either in vivo or in vitro or respectively, to kill cells or to inhibit cell growth upon VEGF-receptor mediated internalization of SLT-VEGF proteins by the cells. Such activity may be assayed by any method known to those of skill in the art including, but not limited to, the assays that measure protein synthesis, receptor binding, autophosphorylation and internalization and assays that assess cytoxic and cytostatic effects by measuring the effect of a test compound on cell proliferation, apoptosis and on protein synthesis.

As used herein, VEGF refers to polypeptides having amino acid sequences of native VEGF proteins, as well as modified sequences, having amino acid substitutions, deletions, insertions or additions of the native protein but retaining the ability to bind to VEGF receptors and to be internalized. Such polypeptides include, but are not limited to, VEGF121, VEGF165, VEGF189, VEGF209. In one embodiment, VEGF may be obtained from a nucleic acid sequence that encodes a mature 121-aa isoform of the human VEGF, coincides with the region of nucleotides 135-478 of the human VEGF sequence that is available from GenBank (accession M32977). This sequence codes for VEGF exons 2-5 followed by the region of nucleotides 611-632 which code for VEGF exon 8 and a stop codon:

(SEQ ID NO:10)
GCACCCATGGCAGAAGGAGGAGGGCAGAATCATCACGAAGTGGTGAAGTT

CATGGATGTCTATCAGCGCAGCTACTGCCATCCAATCGAGACCCTGGTGG

ACATCTTCCAGGAGTACCCTGATGAGATCGAGTACATCTTCAAGCCATCC

TGTGTGCCCCTGATGCGATGCGGGGGCTGCTGCAATGACGAGGGCCTGGA

GTGTGTGCCCACTGAGGAGTCCAACATCACCATGCAGATTATGCGGATCA

AACCTCACCAAGGCCAGCACATAGGAGAGATGAGCTTCCTACAGCACAAC

AAATGTGAATGCAGACCAAAGAAAGATAGAGCAAGACAAGAAAATCCCTG

TGGGCCTTGCTCAGAGCGGAGAAAGCATTTGTTTGTACAAGATCCGCAGA

CGTGTAAATGTTCCTGCAAAAACACAGACTCGCGTTGCAAGGCGAGGCAG

CTTGAGTTAAACGAACGTACTTGCAGATGTGACAAGCCGAGGCGGTGA

It is understood that differences in amino acid sequences can occur among VEGFs of different species as well as among VEGFs from individual organisms or species. Reference to VEGFs is also intended to encompass proteins isolated from natural sources as well as those made synthetically, as by recombinant means or possibly by chemical synthesis. VEGF also encompasses mutants of VEGF that possess the ability to target SLT to VEGF-receptor expressing cells and created in order to, for example, retain or increase the activity or stability of the growth factor, to reduce or eliminate disulfide scrambling, or to alter reactivity with various modifying groups (e.g. polyethylene glycol).

As used herein, the term "VEGF receptor" is used to refer to receptors that specifically interact with VEGF and transport it into the cell. Included, but not limited to, among these are KDR/flk-1 (VEGF-R1), flt-1 (VEGF-R2).

As used herein, the term "polypeptide reactive with the VEGF receptor" refers to any polypeptide that specifically interacts with VEGF receptor, preferably the high-affinity VEGF receptor, and is transported into the cell by virtue of its interaction with the VEGF receptor.

Unless defined otherwise, all additional technical and scientific terms used herein have the same meaning as is commonly understood by one of skill in the art to which the subject matter herein belongs.

Although the invention is by no means limited hereto it will be exemplified in the following mainly with reference to the full length A subunit of Shiga-like bacterial toxin (SLT/L), truncated version thereof (SLT/S), or a catalytically inactive double mutant version thereof (SLT/Lci). Accordingly, the invention will be described in relation to the construction of genetic fusion proteins between SLT/L, or SLT/S, or SLT/Lci and VEGF molecule which will target the fusion protein to specific VEGF receptors, and it will be demonstrated herein that only fusion proteins containing SLT/L or SLT/S, but not SLT/Lci, exhibit cytotoxic and/or cytostatic effects on endothelial cells.

Fusion proteins denoted SLT-VEGF/L and SLT-VEGF/S consisting of SLT/L or SLT/S linked to VEGF121 inhibit growth of porcine endothelial cells PAE/KDR cells overexpressing KDR/flk-1 receptor for VEGF in a dose-dependent manner with $IC_{50}$ of ~0.15 nM. At the low nanomolar concentration range SLT-VEGF/L proteins are cytotoxic, killing virtually all PAE/KDR cells after exposure to concentration as low as 2.5 nM. In contrast, SLT-VEGF/S proteins at the low nanomolar concentrations are mostly cytostatic. These effects depend on catalytic activity of SLT moiety in fusion protein that inactivates ribosomes, because catalytically inactive VEGF-SLT/Lci does not affect PAE/KDR cell growth. These effects depend on expression of KDR/flk-1 receptors, because SLT-VEGF/L and SLT-VEGF/S do not affect growth of porcine endothelial cells PAE/V cells that do not express KDR/flk-1 receptors but transfected by control vector. Importantly, SLT-VEGF/L proteins do not affect endothelial cells that express low numbers of KDR/flk-1 receptors or quiescent PAE/KDR cells even at concentration as high as 20 nM. The results demonstrate that SLT-VEGF/L and SLT-VEGF/S molecules can enter cells via KDR/flk-1 receptors, and SLT/L or SLT/S moieties of said molecules can effectively cause cytotoxic and/or cytostatic effects in growing endothelial cells overexpressing KDR/flk-1 receptors, but not in endothelial cells that express low numbers of KDR/flk-1 receptors or quiescent endothelial cells.

These results demonstrate the possibility of using SLT-VEGF/L and SLT-VEGF/S proteins to target selectively growing endothelial at the sites of angiogenesis that are known to overexpress KDR/flk-1 receptors, without affecting normal endothelial cells or other types of cells that express either low number or none receptors for VEGF proteins, thereby minimizing undesired side effects that might arise from interaction with not-targeted cells. Therefore, SLT-VEGF/L and SLT-VEGF/S proteins are given a narrow spectrum of cellular interactions via specific binding to surface VEGF receptors in cells overexpressing said receptors thereby targeting SLT/L and SLT/S to primarily growing endothelial cells at the sites of angiogenesis.

Furthermore, using SLT-VEGF/L and SLT-VEGF/S constructs we have demonstrated that:

(i) SLT-VEGF/L and SLT-VEGF/S but not SLT-VEGF/Lci proteins retain the ability to inhibit protein synthesis.

(ii) SLT-VEGF/L, SLT-VEGF/Lci, and SLT-VEGF/S proteins bind to cellular KDR/flk-1 receptors and induce tyrosine autophosphorylation of said receptors.

(iii) SLT-VEGF/L protein is cytotoxic protein inducing death of growing endothelial cells that overexpress KDR/flk-1 receptors, but not endothelial cells that express low number of KDR/flk-1 receptors, or quiescent endothelial cells, while SLT-VEGF/S is mostly cytostatic protein causing growth inhibition.

The compositions for use in inhibition of endothelial cell growth in order to inhibit angiogenesis comprise a fusion protein, in combination with a pharmaceutically acceptable diluent or carrier. The compositions according to the invention will in practice normally be administered by intravenous injection, continuous infusion, although other methods, such as parenternal injection or intramuscular injection may also be used.

Compositions for injection can be provided in unit dose form and can take a form such as solution and can contain formulating agents, such as stabilizing agents, buffers, and the like.

The invention is further described by the following Examples, but is not intended to be limited by the Examples. All parts and percentages are by weight and all temperatures are in degrees Celsius unless explicitly stated otherwise.

EXAMPLES

Example 1

Construction of DNA Sequences Encoding SLT-VEGF/L and SLT-VEGF/S Fusion Proteins General Descriptions Bacterial Strains, Plasmids, and Mammalian Cells

*E. coli* strain DH5α is commercially available from Life Technologies, Inc. (USA) *E. coli* strains BL21 (DE3) pLysS and Origami (DE3) pLysS are commercially available from Novagen. Vector pET32(a) for bacterial expression of recombinant proteins with a terminal extension containing His-tag, S-tag, and thioredoxin is commercially available from Novagen (USA). Plasmid pLen-121 containing the DNA sequence encoding the 121-residue form of human VEGF has been described in U.S. Pat. No. 5,219,739, herein incorporated by reference in it's entirety, and was obtained from Dr. J. Abraham (Scios Nova, Inc., USA). Plasmid pJB144 containing a sequence for VT1/SLT holotoxin was obtained from Dr. J. Brunton (Samuel Lunenfield Research institute, Toronto, Canada). Plasmids pBalPst (empty vector) and pBalPst/KDR encoding KDR/flk-1 receptor were obtained from Dr. B. Terman (Albert Einstein School of Medicine, New York City, USA). Porcine aortic endothelial (PAE) cells and 293 human primary embryonic kidney cells (293) were obtained from American Type Culture Collection (USA). PAE cells expressing $2-3 \times 10^5$ KDR/flk-1 per cell (PAE/KDR), PAE cells transfected with pBalPst plasmid (PAE/V), human umbilical vein endothelial (HUVE) cells and MS1 mouse endothelial cells were obtained from Dr. B. Terman (Albert Einstein School of Medicine, New York City, USA). 293 cells overexpressing VEGFR-2 (293/KDR) and PAE cells expressing a low number of KDR/flk-1 ($PAE/KDR_{low}$) were constructed by transfection of the corresponding parental cells with pBalPst/KDR plasmid using TransIT-LT1 reagent (PanVera Corporation, USA), followed by selection in the presence of 0.375 μg/ml puromycin. A clone of 293/KDR cells chosen for this study expressed $2.5 \times 10^6$ VEGFR-2 per cell according to Scatchard's analysis of $^{125}$I-VEGF165 binding. Expression levels of VEGFR-2 in PAE/KDR and $PAE/KDR_{low}$ cells were estimated by Western blot analysis with 293/KDR cells serving as a standard. The immunoblots were probed with rabbit polyclonal anti-VEGFR-2 serum obtained from Dr. B. Terman (Albert Einstein School of Medicine, New York City, USA). PAE, 293 cells, and their derivatives were maintained in DMEM supplemented with 10% fetal bovine serum (Gemini, Inc., USA), 2 mM L-glutamine and antibiotics. Low passage number HUVE cells ($3^{rd}$-$7^{th}$ passages) were grown in gelatin-coated flasks in DMEM with 20% FBS, 50 ng/ml basic fibroblast growth factor, 100 μg/ml heparin, 2 mM L-glutamine and antibiotics. MS1 cells are grown in DMEM with 5% FBS, 4 mM L-glutamine and antibiotics. All cell lines were cultivated at 37° C., 5% $CO_2$.

DNA Manipulations

The restriction and modification enzymes employed herein are commercially available from the usual sources and were used according to manufacturer's instructions. The sequencing of the different DNA constructs was done at Macromolecular Resources (Department of Biochemistry and Molecular Biology, Ft. Collins, Colo., USA). Competent cells, transformation, and bacterial media were prepared according to Sambrook et al. (J. Sambrook, E. F. Fritsch and T. Maniatis. (1989) Molecular Cloning: A Laboratory Manual, Cold Spring Harbor Laboratory Press, Cold Spring Harbor, N.Y.), or according to the manufacturer's instructions. Purification of plasmids was done using Wizard Plus SV Minipreps or Maxipreps DNA Purification Systems (Promega, USA) according to the manufacturer's instructions. Further purification of DNA as well as purification of DNA from agarose gels was done using the Geneclean Spin kit (Bio 101, USA) according to the manufacturer's instructions.

Sub-Cloning of 121-Residue Isoform of Human VEGF into a PET32 (a) Expression Vector.

Primers for Amplification of DNA Encoding 121-Residue Isoform of Human VEGF

Primers for human VEGF DNA amplifications were synthesized by GeneLink (USA). The primer corresponding to the "sense" strand (SEQ ID NO:1) included a Stu I restriction site immediately upstream of the DNA codon for amino acid-1 of the mature 121-residue isoform of VEGF. The primer corresponding to the "antisense" strand (SEQ ID NO:2) complemented the coding sequence of the DNA encoding the carboxyl end of the mature peptide, including a translation stop codon after the sequence encoding mature VEGF, and introduced an Xho I restriction site downstream of the VEGF-encoding DNA and the stop codon.

5'- TAAGGCCTATGGCAGAAGGAGGAGGG -3'   (SEQ ID NO:1)

5'- ACTCGAGTCACCGCCTCGGCTTGTCAC -3'   (SEQ ID NO:2)

PCR to Amplify DNA Encoding 121-Residue Isoform of Human VEGF

The human VEGF cDNA was amplified by PCR from the pLen-121 plasmid containing the sequence for the 121-residue isoform of human VEGF. Ten nanograms of template DNA were mixed in a 0.1 ml reaction mixture, containing 10 pmol of each oligonucleotide, 0.2 mM of each dNTP and 2 U of Pfu polymerase (Stratagene, USA) in Pfu buffer (Stratagene, USA). Incubations were done in a DNA GenAmp PCR System 2400 (Perkin Elmer Cetus, USA). One cycle included a denaturation step (94° C. for 1 min.), an annealing step (65° C. for 1 min), and an elongation step (72° C. for 1 min). The amplified DNA was digested with Stu I and Xho I and purified with the Geneclean Spin kit (BIO 101, USA).

pET32-VEGF121 Plasmid Construction

Amplified DNA forms described above were ligated into a pET32(a) vector using Xho I site from multiple cloning site of the vector and Stu I site, which was constructed by treating the vector as follows: pET32(a) DNA was linearized with Nco I restrictase, and one of produced recessed terminus was partially filled with cytidine using DNA polymerase I Large (Klenow) fragment. The construct was purified with the Geneclean Spin kit (BIO 101, USA) and single-stranded overhangs were removed with mung bean nuclease. The resulted construct was digested with Xho I restrictase and purified with the Geneclean Spin kit (BIO 101, USA). The ligation was accomplished such that the first amino acid of the mature 121-residue isoform of VEGF became the first amino acid after an enterokinase cleavage site provided by vector. The resulting plasmid was designated pET32-txVEGF121 and was transformed into DH5α competent cells (Life Technologies, USA) according to the manufacturer's instructions.

The bacterial culture containing the desired plasmid was grown further in order to obtain large preparations of isolated plasmid using methods described above.

Figure 1:
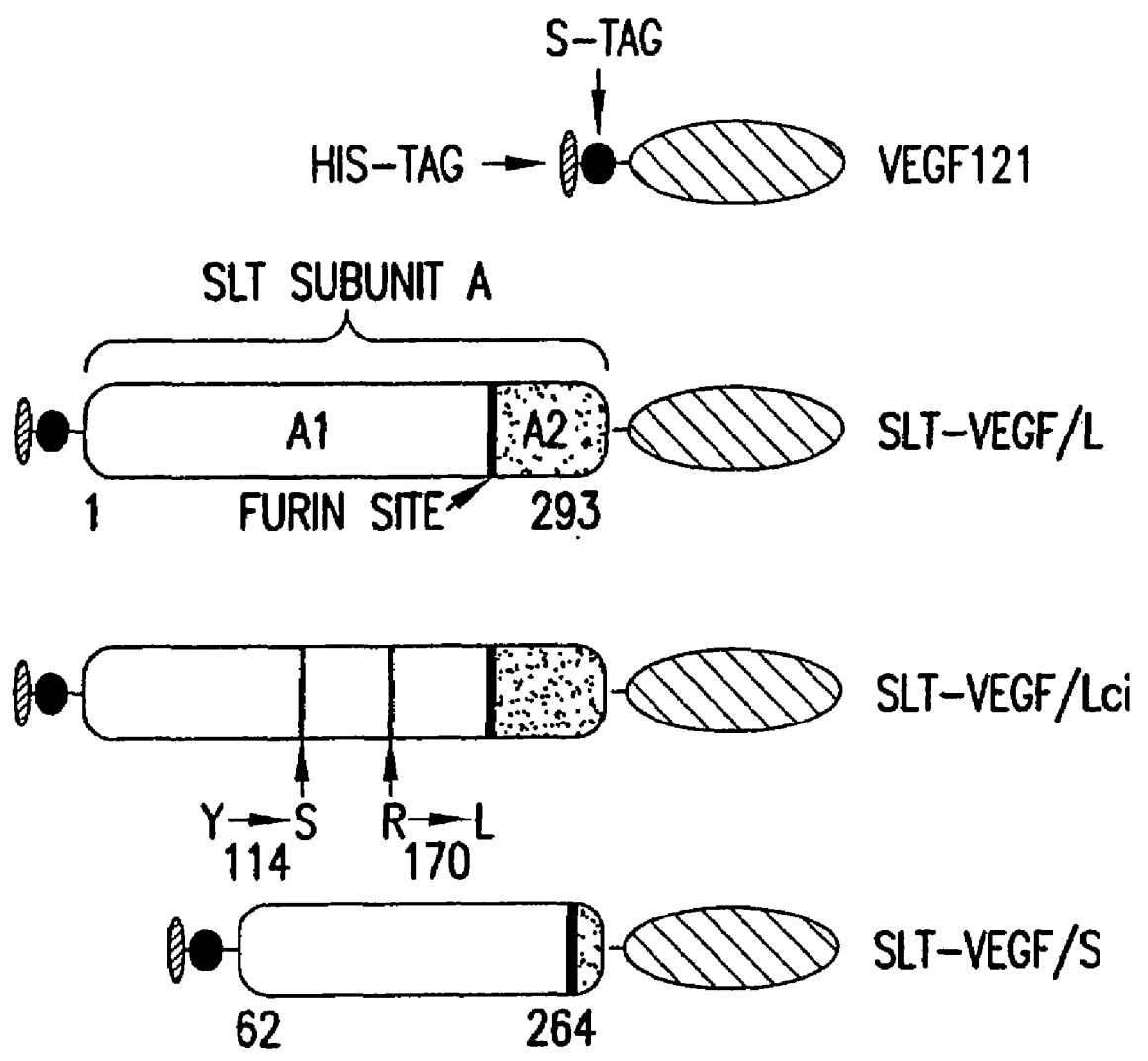

The thioredoxin (tx) gene was removed from the pET32-txVEGF121 by digestion of the purified plasmid DNA with restrictase Nde I, followed by intramolecular ligation of the linearized plasmid DNAs with T4 ligase. The resulting plasmid was designated pET32-VEGF121 and was transformed into DH5α competent cells (Life Technologies, USA) according to the manufacturer's instructions. The bacterial culture containing the desired plasmid was grown further in order to obtain large preparations of isolated plasmid using methods described above. Plasmid pET-VEGF121 DNA encodes a 36 amino-acids full-length N-terminus, containing His-tag (6 amino acids), trombin cleavage site (6 amino acids), S-tag (15 amino acids), a 6-amino acid full-length connecting peptide containing enterokinase cleavage site, and 1 to 121 amino acids of the mature VEGF121 protein (FIG. 1).

Sub-Cloning of Full-Length, Truncated and Mutant Forms of SLT Subunit A into pET32-VEGF121 Vector 1. Primers for Amplification of DNA Encoding Full-Length (L) and Truncated (S) Forms of SLT Subunit A.

Primers for DNA amplifications of DNA encoding L and S forms of SLT subunit A were synthesized by GeneLink (USA). The primers corresponding to the "sense" strands of full-length (293-residue) SLT form (SEQ ID NO:3) and truncated (202-residue) SLT form (SEQ ID NO:4) included Bgl II restriction sites upstream of the DNA codon for amino acid-1 and amino acid-62, respectively, of the mature SLT subunit A. In order to clone SLT molecules in frame with the first Met of VEGF121 an additional G was inserted between the Bgl II sites and the ORFs of SLT:

```
                                         (SEQ ID NO:3)
5'- CCGAGATCTGAAGGAATTTACCTTAGAC -3'

(SEQ ID NO:4)
5'- CCCAGATCTGCTACGGCTTATTGTTGAACG -3'
```

The primer corresponding to the "antisense" strand of full-length SLT form complemented the coding sequence of the SLT DNA encoding the carboxyl end of the mature SLT subunit A right upstream the stop codon (SEQ ID NO:5). The primer corresponding to the "antisense" strand of truncated SLT form complemented the coding sequence of the DNA encoding the DNA codons for amino acids 258-264 of SLT subunit A (SEQ ID NO:6). Both primers introduced Kpn I restriction sites downstream of the SLT-encoding DNA:

```
5'- ATAGGTACCACTGCTAATAGTTCTGCG -3'    (SEQ ID NO:5)

5'- ATAGGTACCATCTGCCGGACACATAGAAG -3'  (SEQ ID NO:6)
```

PCR to Amplify Full-Length and Truncated Forms of SLT Subunit A

DNA encoding full-length and truncated forms of SLT Subunit A were amplified by PCR from the plasmid pJB144 containing VT1/SLT holotoxin. Ten nanograms of template DNA were mixed in a 0.1 ml reaction mixture, containing 10 pmol of each oligonucleotide, 0.2 mM dNTPs and 2 U of Vent DNA polymerase (New England Biolabs, USA) in Vent buffer. Incubations were done in a DNA GenAmp PCR System 2400 (Perkin Elmer Cetus, USA). One cycle included a denaturation step (94° C. for 30 sec.), an annealing step (58° C. for 1 min), and an elongation step (72° C. for 1 min 20 sec).

After 25 cycles, a 10 µl aliquot of each reaction was run on a 1% agarose gel to verify the correct size of the amplified product. The amplified DNA forms were digested with Bgl II and Kpn I restrictases and purified with the Geneclean Spin kit (BIO 101, USA).

pET32-VEGF121-SLT/L and pET32-VEGF121-SLT/S Plasmids Construction

Amplified SLT DNA forms described above were ligated into pET32-VEGF121 vector that had been treated with Bgl II and Kpn I restrictases and purified as described above. The resulting plasmids containing DNA encoding full-length and truncated SLT forms were designated pET32-VEGF121-SLT/L and pET32-VEGF121-SLT/S, respectively, and transformed into DH5α competent cells (Gibco, USA) according to the manufacturer's instructions. The clones were screened, purified, characterized and propagated as described above. The DNA fragments in pET32-VEGF121-SLT/L and pET32-VEGF121-SLT/S plasmids were sequenced from T7 promoter to nucleotide 203 in the coding sequences of SLT in order to confirm that they contain expected SLT DNA sequences.

Plasmid pET-VEGF121-SLT/L DNA encodes a 36 amino-acids full-length N-terminus, containing His-tag (6 amino acids), thrombin cleavage site (6 amino acids), S-tag (15 amino acids), the entire SLT subunit A (293 amino acids), a 6-amino acid full-length connecting peptide containing enterokinase cleavage site, and 1 to 121 amino acids of the mature VEGF121 protein (FIG. 1). Plasmid pET-VEGF121-SLT/S is identical to the plasmid pET-VEGF121-SLT/L, but instead the DNA encoding the entire SLT subunit A it contains the DNA encoding a 202-amino acid fragment of this subunit from amino acid 62 to amino acid 264 (FIG. 1).

According to the present invention, plasmid pET-VEGF121-SLT/L contains the following unique nucleic acid sequence:

(SEQ ID NO:11)

```
ATGCACCATCATCATCATCATTCTTCTGGTCTGGTGCCACGCGGTTCTGG

TATGAAAGAAACCGCTGCTGCTAAATTCGAACGCCAGCACATGGACAGCC

CAGATCTGAAGGAATTTACCTTAGACTTCTCGACTGCAAAGACGTATGTA

GATTCGCTGAATGTCATTCGCTCTGCAATAGGTACTCCATTACAGACTAT

TTCATCAGGAGGTACGTCTTTACTGATGATTGATAGTGGCACAGGGGATA

ATTTGTTTGCAGTTGATGTCAGAGGGATAGATCCAGAGGAAGGGCGGTTT

AATAATCTACGGCTTATTGTTGAACGAAATAATTTATATGTGACAGGATT

TGTTAACAGGACAAATAATGTTTTTTATCGCTTTGCTGATTTTTCACATG

TTACCTTTCCAGGTACAACAGCGGTTACATTGTCTGGTGACAGTAGCTAT

ACCACGTTACAGCGTGTTGCAGGGATCAGTCGTACGGGGATGCAGATAAA

TCGCCATTCGTTGACTACTTCTTATCTGGATTTAATGTCGCATAGTGGAA

CCTCACTGACGCAGTCTGTGGCAAGAGCGATGTTACGGTTTGTTACTGTG

ACAGCTGAAGCTTTACGTTTTCGGCAAATACAGAGGGGATTTCGTACAAC

ACTGGATGATCTCAGTGGGCGTTCTTATGTAATGACTGCTGAAGATGTTG

ATCTTACATTGAACTGGGGAAGGTTGAGTAGCGTCCTGCCTGACTATCAT

GGACAAGACTCTGTTCGTGTAGGAAGAATTTCTTTTGGAAGCATTAATGC

AATTCTGGGAAGCGTGGCATTAATACTGAATTGTCATCATCATGCATCGC
```

-continued

```
GAGTTGCCAGAATGGCATCTGATGAGTTTCCTTCTATGTGTCCGGCAGAT

GGAAGAGTCCGTGGGATTACGCACAATAAAATATTGTGGGATTCATCCAC

TCTGGGGGCAATTCTGATGCGCAGAACTATTAGCAGTGGGTACCGACGAC

GACGACAAGGCACCCATGGCAGAAGGAGGAGGGCAGAATCATCACGAAGT

GGTGAAGTTCATGGATGTCTATCAGCGCAGCTACTGCCATCCAATCGAGA

CCCTGGTGGACATCTTCCAGGAGTACCCTGATGAGATCGAGTACATCTTC

AAGCCATCCTGTGTGCCCCTGATGCGATGCGGGGGCTGCTGCAATGACGA

GGGCCTGGAGTGTGTGCCCACTGAGGAGTCCAACATCACCATGCAGATTA

TGCGGATCAAACCTCACCAAGGCCAGCACATAGGAGAGATGAGCTTCCTA

CAGCACAACAAATGTGAATGCAGACCAAAGAAAGATAGAGCAAGACAAGA

AAATCCCTGTGGGCCTTGCTCAGAGCGGAGAAAGCATTTGTTTGTACAAG

ATCCGCAGACGTGTAAATGTTCCTGCAAAAACACAGACTCGCGTTGCAAG

GCGAGGCAGCTTGAGTTAAACGAACGTACTTGCAGATGTGACAAGCCGAG

GCGGTGA
```

The above nucleic acid sequence (SEQ ID NO:11) is a combination of known sequences which, together, produce a unique nucleic acid sequence. The above sequence includes a 5'-terminal sequence that encodes an initial MET, a 6× his-tag, a thrombin cleavage site, a bovine s-tag, and a Bgl II restriction site, and coincides with the region of nucleotides 343-241 of the PET32a (+) vector DNA which is commercially available from Novagen, Inc. That portion of the sequence is as follows:

(SEQ ID NO:12)

```
ATGCACCATCATCATCATCATTCTTCTGGTCTGGTGCCACGCGGTTCTGG

TATGAAAGAAACCGCTGCTGCTAAATTCGAACGCCAGCACATGGACAGCC

CAGATCT
```

A single nucleotide insertion, G, shifts the open reading frame due to cloning into BglII site. Next, a sequence includes a sequence that codes for the mature SLT-1 A-subunit and coincides with the region of nucleotides 67-945 of the SLT A-subunit sequence from Genbank (Accession No. AB015056). This portion of the sequence is shown as SEQ ID NO:9 above:

(SEQ ID NO:9)

```
AAGGAATTTACCTTAGACTTCTCGACTGCAAAGACGTATGTAGATTCGCT

GAATGTCATTCGCTCTGCAATAGGTACTCCATTACAGACTATTTCATCAG

GAGGTACGTCTTTACTGATGATTGATAGTGGCACAGGGGATAATTTGTTT

GCAGTTGATGTCAGAGGGATAGATCCAGAGGAAGGGCGGTTTAATAATCT

ACGGCTTATTGTTGAACGAAATAATTTATATGTGACAGGATTTGTTAACA

GGACAAATAATGTTTTTTATCGCTTTGCTGATTTTTCACATGTTACCTTT

CCAGGTACAACAGCGGTTACATTGTCTGGTGACAGTAGCTATACCACGTT

ACAGCGTGTTGCAGGGATCAGTCGTACGGGGATGCAGATAAATCGCCATT

CGTTGACTACTTCTTATCTGGATTTAATGTCGCATAGTGGAACCTCACTG

ACGCAGTCTGTGGCAAGAGCGATGTTACGGTTTGTTACTGTGACAGCTGA
```

-continued

```
AGCTTTACGTTTTCGGCAAATACAGAGGGGATTTCGTACAACACTGGATG

ATCTCAGTGGGCGTTCTTATGTAATGACTGCTGAAGATGTTGATCTTACA

TTGAACTGGGGAAGGTTGAGTAGCGTCCTGCCTGACTATCATGGACAAGA

CTCTGTTCGTGTAGGAAGAATTTCTTTTGGAAGCATTAATGCAATTCTGG

GAAGCGTGGCATTAATACTGAATTGTCATCATCATGCATCGCGAGTTGCC

AGAATGGCATCTGATGAGTTTCCTTCTATGTGTCCGGCAGATGGAAGAGT

CCGTGGGATTACGCACAATAAAATATTGTGGGATTCATCCACTCTGGGGG

CAATTCTGATGCGCAGAACTATTAGCAGT
```

A sequence coding for a Kpn II restriction site and an enterokinase cleavage site follows this sequence, and coincides with the region of nucleotides 240-219 of the PET32a (+) vector DNA (available commercially from Novagen). That portion of the sequence is as follows:

```
    GGGTACCGACGACGACGACAAG.         (SEQ ID NO:13)
```

Finally, the sequence includes a 3'-terminal sequence that encodes the mature 121-aa isoform of the human VEGF. This sequence coincides with the region of nucleotides 135-478 of the human VEGF sequence from Genbank (Accession No. M32977), and codes for VEGF exons 2-5 followed by the region of nucleotides 611-632 coding for VEGF exon 8 and a stop codon. That sequence is as follows:

```
                                        (SEQ ID NO:10)
GCACCCATGGCAGAAGGAGGAGGGCAGAATCATCACGAAGTGGTGAAGTT

CATGGATGTCTATCAGCGCAGCTACTGCCATCCAATCGAGACCCTGGTGG

ACATCTTCCAGGAGTACCCTGATGAGATCGAGTACATCTTCAAGCCATCC

TGTGTGCCCCTGATGCGATGCGGGGCTGCTGCAATGACGAGGGCCTGGA

GTGTGTGCCCACTGAGGAGTCCAACATCACCATGCAGATTATGCGGATCA

AACCTCACCAAGGCCAGCACATAGGAGAGATGAGCTTCCTACAGCACAAC

AAATGTGAATGCAGACCAAAGAAAGATAGAGCAAGACAAGAAAATCCCTG

TGGGCCTTGCTCAGAGCGGAGAAAGCATTTGTTTGTACAAGATCCGCAGA

CGTGTAAATGTTCCTGCAAAAACACAGACTCGCGTTGCAAGGCGAGGCAG

CTTGAGTTAAACGAACGTACTTGCAGATGTGACAAGCCGAGGCGGTGA
```

Construction of Plasmid for Expression of Catalytically Inactive SLT-VEGF/Lci Protein.

Site-specific mutagenesis of SLT-1 A-subunit encoded by pET32/SLT-VEGF/L was done using GeneEditor™ in vitro Site-Directed Mutaganesis System (Promega). Two mutagenic primers were designed to introduce three point mutations (underlined): Y114S (SEQ ID NO:7), and E167Q and R170L (SEQ ID NO:8):

```
                                            (SEQ ID NO:7)
5'- ACGTGGTAGAGCTACTGTCACC -3'

(SEQ ID NO:8)
5'- TTGCCGAAAAAGTAAAGCTTGAGCTGTCACAG -3'
```

The Y114S and R170L mutations were confirmed by sequencing of mutated DNA isolated from two clones. The E167Q mutation was not detected in either clone. The resulting plasmid designated pET32-VEGF121-SLT/Lci is identical to plasmid pET-VEGF121-SLT/L, but instead the DNA encoding wild type SLT subunit A it contains the DNA encoding a double mutant (Y114S and R170L) of this subunit (FIG. 1).

Example 2

Expression and Purification of Recombinant SLT-VEGF/L, SLT-VEGF/Lci, and SLT-VEGF/S Fusion Proteins A. Expression of SLT-VEGF/L, SLT-VEGF/Lci, and SLT-VEGF/S Proteins 1. Expression of SLT-VEGF/L and SLT-VEGF/S Proteins in *E. Coli* BL21 (DE3) pLysS The pET-VEGF121-SLT/L and pET-VEGF121-SLT/S transformed *E. coli* cells BL21 (DE3) pLysS (Novagen, USA) were grown under conditions in which the expression of the fusion proteins is repressed by the lac repressor to an O.D. in or at the middle of the log phase of growth after which IPTG (isopropyl-β-D-thiogalactoside, Life Technologies, USA) was added to induce expression of the fusion protein-encoding DNA.

To generate a large-batch culture of pET-VEGF121-SLT/L and pET-VEGF121-SLT/S transformed *E. coli* cells, an overnight cultures (lasting approximately 16 hours) of BL21 (DE3) pLysS *E. coli* cells transformed with the plasmids pET-VEGF121-SLT/L and pET-VEGF121-SLT/S, respectively, in LB broth containing 50 mg/L ampicillin and 34 mg/L chloramphenicol was diluted 1:100 into a flask containing 100 ml LB broth with 50 mg/L ampicillin and 34 mg/L chloramphenicol. Cells were grown with shaking at 37° C. until the optical density at 600 nm reached 0.5 as measured in a spectrophotometer (Ultrospec 1000, Pharmacia Biotech, USA).

In the second step, fusion protein expression was induced by the addition of IPTG (Life Technologies, USA) to a final concentration of 1 mM. Induced cultures were grown for 3.5 additional hours for SLT-VEGF/L and 2 additional hours for SLT-VEGF/S; then harvested by centrifugation (25 min., 5000×g). The cell pellets were resuspended in the ice-cold buffer A (50 mM Tris-HCl, pH 7.5, 0.1 M $MgCl_2$, 1% Nonidet P 40, 0.1 M DTT, 200 mg/L PMSF, 25 mg/L antitrypsin, 50 mg/L leupeptin, 25 mg/L aprotinin). After five cycles of freezing and thawing, DNAse was added to each of the cell suspensions to 50 Upper ml. The suspensions were incubated for 20 min at room temperature, then centrifuged at 5,000×g for 30 min at 4° C. Analysis of distribution of fusion proteins designated as SLT-VEGF/L and SLT-VEGF/S between soluble fractions and inclusion bodies of IPTG-induced bacteria indicated that SLT-VEGF/L and SLT-VEGF/S fusion proteins were present in the inclusion bodies (FIG. 2, panel A).

The inclusion body pellets were washed with the buffer containing 20 mM Tris-HCL, pH 8.0, 0.5 M NaCl, 5 mM imidazole, and solubilized in 8 M urea, followed by sonication of the solutions for 5-10 min in an ice-cold water sonicator (FC 14, Fisher Sci., USA). The protein solutions were clarified by centrifugation at 14×g for 10 min at 4° C. and the supernatants were collected and dialyzed against a 1000-fold volume of the buffer containing 10 mM Tris-HCl, pH 8.0, 150 mM NaCl, 0.05% Nonidet P 40 for 16 hours at 4° C. The SLT-VEGF/L and SLT-VEGF/S fusion protein solutions were supplemented with 10% glycerol and stored in aliquots at −20° C. The concentrations of recombinant proteins were determined with S-tag assay kit (Novagen, USA) according to manufacturer's instructions.

2. Expression of SLT-VEGF/L, SLT-VEGF/Lci, and SLT-VEGF/S Proteins in *E. coli* Origami (DE3) pLysS The pET-VEGF121-SLT/L,SLT-VEGF/Lci, and pET-VEGF121-SLT/S transformed *E. coli* cells Origami (DE3) pLysS (Novagen, USA) were grown under conditions in which the expression of the fusion proteins is repressed by the lac repressor to an O.D. in or at the middle of the log phase of growth after which IPTG (Life Technologies, USA) was added to induce expression of the fusion protein-encoding DNA.

To generate a large-batch culture of pET-VEGF121-SLT/L, pET-VEGF121-SLT/L/ci, and pET-VEGF121-SLT/S transformed *E. coli* cells, an overnight cultures (lasting approximately 16 hours) of Origami (DE3) pLysS *E. coli* cells transformed with the plasmids pET-VEGF121-SLT/L, or pET-VEGF121-SLT/L/ci, or pET-VEGF121-SLT/S, respectively, in LB broth containing 50 mg/L ampicillin, 34 mg/L chloramphenicol, 12.5 mg/L tetracyclin, and 15 mg/L kanamycin was diluted 1:100 into a flask containing 100 ml LB broth with 50 mg/L ampicillin, 34 mg/L chloramphenicol, 12.5 mg/L tetracyclin, and 15 mg/L kanamycin. Cells were grown with shaking at 37° C. until the optical density at 600 nm reached 0.4 measured in a spectrophotometer (Ultrospec 1000, Pharmacia Biotech, USA).

Figure 2A:
FIG. 2 illustrates expression of SLT-VEGF/L, and SLT-VEGF/S proteins in BL21 (DE3) pLysS and Origami (DE3) pLysS E. coli strains (termed BL21 and Origami, respectively) and their accumulation in inclusion bodies isolated from respective hosts (FIG. 2, panels A and B).
Figure 2B:
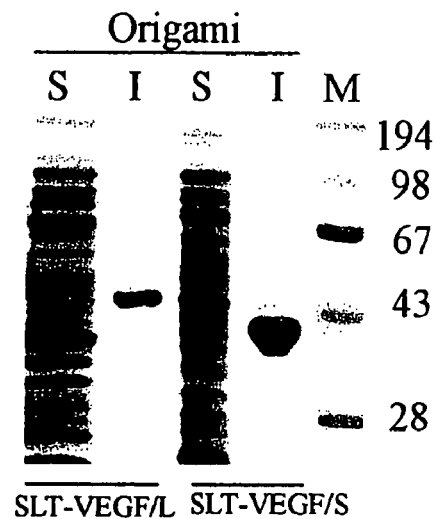
Figure 2C:
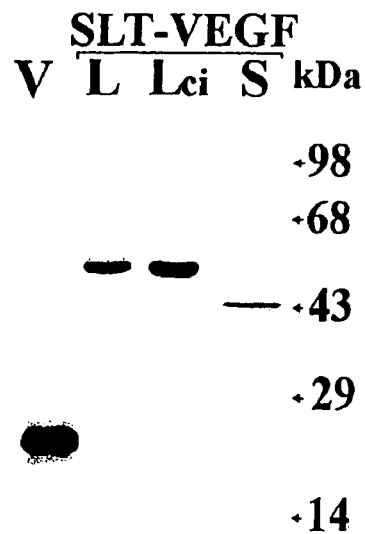
Figure 3A:
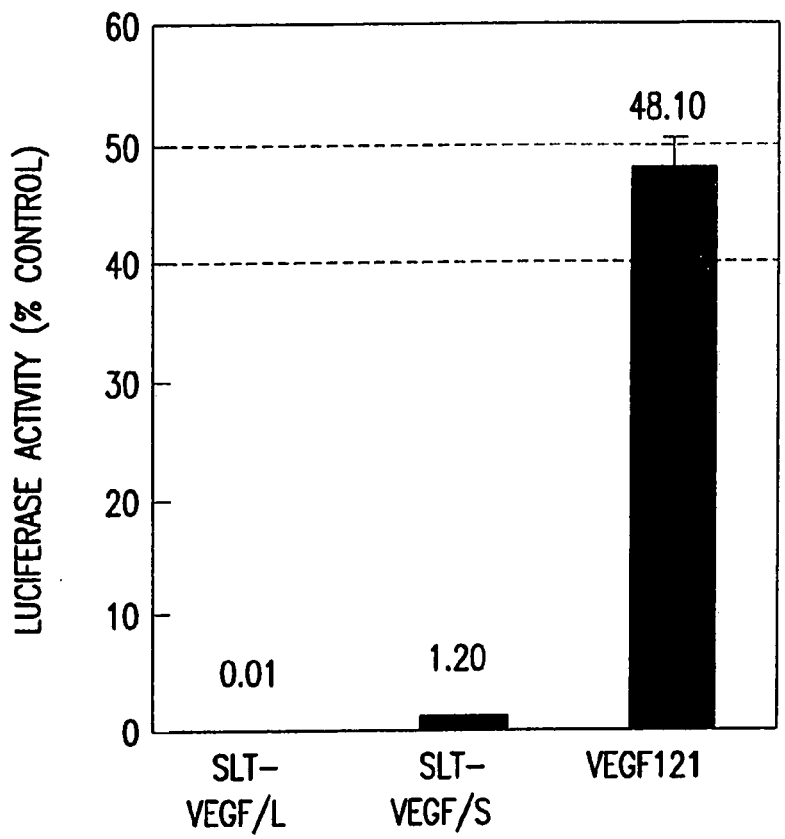
FIG. 3 illustrates that SLT-VEGF/L and SLT-VEGF/S proteins, but not catalytically inactive SLT-VEGF/Lci, inhibit protein synthesis in cell-free translation system. SLT-VEGF/L and SLT-VEGF/S fusion proteins inhibit translation of firefly luciferase mRNA by 99.99% and 99%, respectively at concentration of 100 nM (FIG. 3, panel A). Recombinant VEGF121 protein isolated by the same procedure as SLT-VEGF fusion proteins inhibits translation only ~50% at concentration as high as 1,000 nM (FIG. 3, panel A). SLT-VEGF/L and SLT-VEGF/S inhibited protein synthesis in a dose-dependent manner with 90% inhibition at concentrations 0.04 nM and 2 nM, respectively, while SLT-VEGF/Lci did not inhibit protein synthesis (FIG. 3, panel B). Detected luciferase activities in percents of the VEGF121 control are indicated.
Figure 3B:
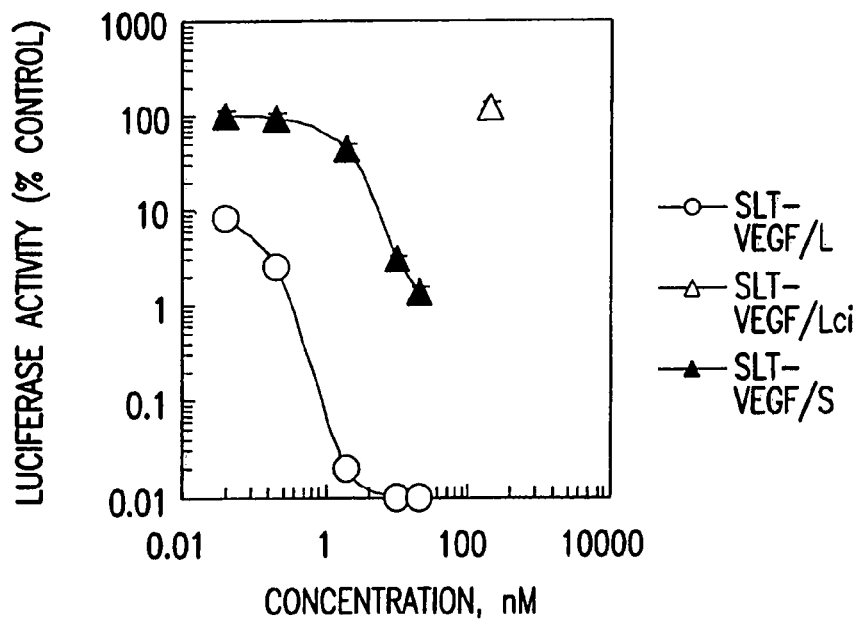

In the second step, fusion protein expression was induced by the addition of IPTG (Life Technologies, USA) to a final concentration of 1 mM. Induced cultures were grown for 4 additional hours at 30° C.; then harvested by centrifugation (25 min, 5000×g). The cell pellets were resuspended in the ice-cold buffer A (50 mM Tris-HCl, pH 7.5, 0.1 M $MgCl_2$, 1% Nonidet P 40, 0.1 M DTT, 200 mg/L PMSF, 25 mg/L antitrypsin, 50 mg/L leupeptin, 25 mg/L aprotinin). After five cycles of freezing and thawing, DNAse was added to each of the cell suspensions to 50 U per ml. The suspensions were incubated for 20 min at room temperature; then centrifuged at 5,000 xg for 30 min at 4° C. Analysis of distribution of fusion proteins designated as SLT-VEGF/L, SLT-VEGF/Lci, and SLT-VEGF/S between soluble fractions and inclusion bodies of IPTG-induced bacteria indicated that SLT-VEGF/L and SLT-VEGF/S these proteins were present in the inclusion bodies (FIG. 2, panel B for SLT-VEGF/L and SLT-VEGF/S).

The inclusion body pellets were washed with the buffer containing 20 mM Tris-HCL, pH 8.0, 0.5 M NaCl, 5 mM imidazole, and solubilized in 8 M urea, followed by sonication of the ice-cold solutions for 20-30 sec in a sonicator VirSonic 475 (VirTis, USA) operated at 40-50% of output power. The protein solutions were clarified by centrifugation at 14,000×g for 10 min at 4° C. and the supernatants were collected and dialyzed against a 1000-fold volume of the buffer containing 10 mM Tris-HCl, pH 8.0, 150 mM NaCl, 0.01% Brij-35 for 2 hours at 4° C. and then for 16 hours at 4° C. against a fresh 1000-fold volume of the same buffer. SLT-VEGF/L, SLT-VEGF/Lci, and SLT-VEGF/S fusion protein obtained through this procedure were characterized by SDS-PAGE (FIG. 2, panel C). The SLT-VEGF/L, SLT-VEGF/Lci, and SLT-VEGF/S fusion protein solutions were supplemented with 5% glycerol and stored in aliquots at −70° C. The concentrations of recombinant proteins were determined with S-tag assay kit (Novagen, USA) according to manufacturer's instructions.

B. Expression of VEGF121 in *E. coli* BL21 (DE3) pLysS

The pET32-VEGF121 transformed *E. coli* cells BL21 (DE3) pLysS were grown and expression of recombinant VEGF designated as VEGF121 was induced under conditions described above. Recombinant VEGF121 was recovered from inclusion bodies as described above and supernatant was dialyzed against a 1000-fold volume of the buffer containing 10 mM Tris-HCl, pH 8.0, 150 mM NaCl for 16 hours at 4° C. The VEGF121 protein solutions were supplemented with 10% glycerol and stored in aliquots at −20° C. The concentrations of recombinant VEGF121 proteins were determined with S-tag assay kit (Novagen, USA) according to manufacturer's instructions.

Example 3

Biochemical Activities of SLT-VEGF/L and SLT-VEGF/S Fusion Proteins

Figure 4:
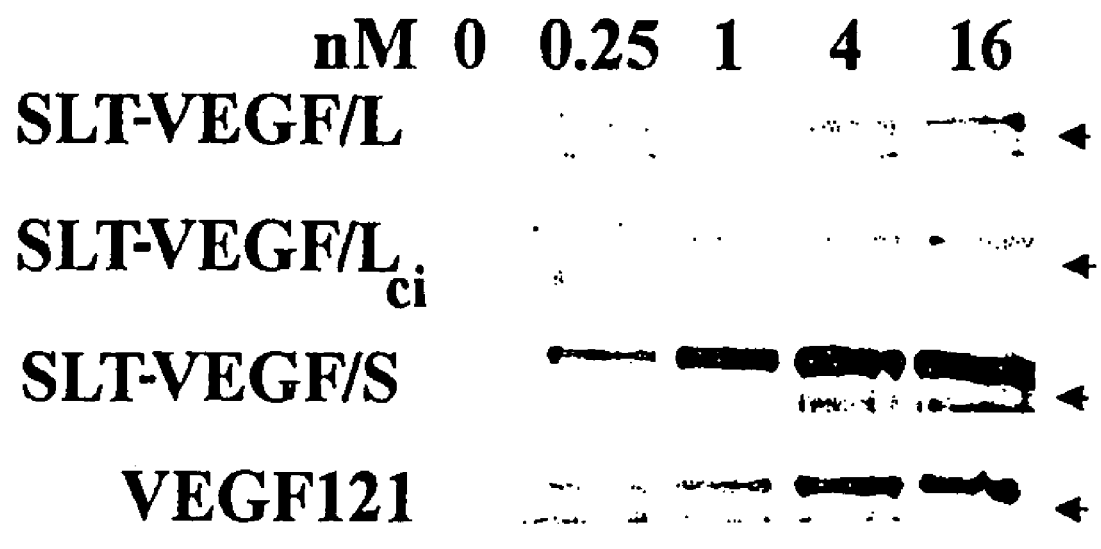
FIG. 4 illustrates that SLT-VEGF/L, SLT-VEGF/Lci, and SLT-VEGF/S proteins induce tyrosine phosphorylation of KDR/flk-1 receptors for VEGF in cells overexpressing KDR/ flk-1 receptors (293/KDR cells). Tyrosine phosphorylation of KDR/flk-1 receptors was detected by Western blot analysis of the lysates of 293/KDR treated with SLT-VEGF/L, SLT-VEGF/Lci, SLT-VEGF/S, and VEGF121, using anti-phosphotyrosine antibody.

A. Inhibitory Effect of SLT-VEGF/L and SLT-VEGF/S Fusion Proteins on Cell-Free Protein Synthesis Abilities of SLT-VEGF/L and SLT-VEGF/S recombinant fusion proteins, obtained above, to inhibit protein synthesis were tested in an in vitro assay measuring cell-free protein synthesis in a nuclease-treated rabbit reticulocyte lysate (Promega, USA). 5 µl of SLT-VEGF/L, SLT-VEGF/S, VEGF121 solutions or storage buffer containing 10 mM Tris-HCL, 150 mM NaCl, 8 mM urea, 10% glycerol were added on ice to 20 μl reaction mixtures that included 18 μl of rabbit reticulocyte lysate, 1 mM complete amino acid mix, 90 mM KCl, and firefly luciferase mRNA, 0.5 μg per assay. The final concentrations of SLT-VEGF/L, SLT-VEGF/S were 100 nM and a final concentration of VEGF121 was 1000 nM. The final concentrations of SLT-VEGF/L, SLT-VEGF/Lci, SLT-VEGF/S in dose-dependence experiments were as indicated in FIG. 3, panel B. After a 90-min incubation at 30° C. the reaction mixtures were diluted 20-fold with water containing 1 mg/ml BSA, and 2 μl of each mixture was assayed for firefly luciferase activity in Luciferase Reaction buffer (Promega, USA) using LumiOne luminometer (Bioscan, Inc, USA) according to the manufacturer's instructions. Luciferase activity of the control reaction containing 100 nM VEGF121 was taken as 100%. SLT-VEGF/L and SLT-VEGF/S fusion proteins at concentration 100 nM inhibited protein synthesis to the levels of 0.01% and 1.2% of control (FIG. 3, panel A). For comparison, recombinant VEGF121 protein at concentration as high as 1000 nM inhibited protein synthesis to the level of 48% of control (FIG. 3, panel A). Dose-dependence experiments revealed that SLT-VEGF/L and SLT-VEGF/S inhibited protein synthesis by 90% at concentrations 0.04 nM and 2 nM, respectively, while SLT-VEGF/Lci did not inhibit protein synthesis (FIG. 3, panel C).

B. Induction of the Tyrosine Phosphorylation of Cellular KDR/flk-1 Receptors by SLT-VEGF/L, SLT-VEGF/Lci, and SLT-VEGF/S Fusion Proteins Abilities of SLT-VEGF/L, SLT-VEGF/Lci, and SLT-VEGF/S recombinant fusion proteins obtained above to induce tyrosine phosphorylation of cellular KDR/flk-1 receptors, was tested using 293 cells stably transfected with KDR/flk-1 designated as 293/KDR cells. About 50,000 293/KDR cells per well were plated onto 24-well plates in 1 ml DMEM (Life Technologies, USA) supplemented with 10% fetal calf serum (Gemini, USA) and incubated overnight at 37° C., 5% $CO_2$. Next day, the cells were washed once with phosphate buffered saline and shifted to DMEM serum-free for 4 hours at 37° C. Subsequently, the medium was changed to serum-free DMEM supplemented with 0.1 mM sodium orthovanadate, 100 ng/ml bovine serum albumine, 25 mM HEPES pH 7.2, and the cells were incubated for 20 min at 37° C. followed by a 20-min incubation at 4° C. Then the cells were incubated with SLT-VEGF/L, or SLT-VEGF/Lci, or SLT-VEGF/S, or VEGF121 for 1 hour at 4° C. followed by 8 min at 37° C. Then the cells were rinsed once with ice-cold phosphate buffered saline containing 0.1 mM sodium orthovanadate, solubilized in sample buffer containing 0.05 M Tris-HCl, pH 6.8, 2.5% SDS, 7.5% glycerol, 5 mM EDTA, 50 mM DTT, 0.025% Bromophenol Blue, and analyzed by Western blotting. Cellular proteins were fractionated by SDS-PAGE on 7.5% gels and were transferred to nitrocellulose (BioRad, USA) using a semi-dry system 2117 Multiphor II (LKB, Sweden), as described by the manufacturer. Western blots were processed and probed with anti-phosphotyrosine RC20:HRP conjugate (Transduction Lab, USA) at dilution 1:2,000 according to the manufacturer's instructions. A chemiluminescence-based system (ECL, Amersham, USA) was used for bands detection. SLT-VEGF/L, SLT-VEGF/Lci, and SLT-VEGF/S proteins induced KDR/flk-1 tyrosine phosphorylation in a dose-dependent manner at the same concentration range as VEGF121. (FIG. 4).

Example 4

Cytotoxic and Cytostatic Effects of SLT-VEGF/L and SLT-VEGF/S Fusion Proteins

A. Effects of VEGF-SLT/L and VEGF-SLT/S Fusion Proteins on Growing Endothelial Cells Overexpressing KDR/flk-1 Receptors and Growing Endothelial Cells that do not Express KDR/flk-1 Receptors Abilities of VEGF-SLT/L and VEGF-SLT/S fusion proteins obtained above to affect growing endothelial cell were tested using porcine aortic endothelial cells stably transfected with KDR/flk-1 (designated as PAE/KDR cells) and porcine aortic endothelial cells stably transfected with the empty vector (designated as PAE/V cells). About 5,000 cells per well were plated onto 24-well plates in 1 ml DMEM (Life Technologies, USA) supplemented with 10% fetal calf serum (Gemini, USA) and incubated overnight at 37° C., 5% $CO_2$. Next day the media was changed to fresh DMEM supplemented with 10% fetal calf serum, and SLT-VEGF/L or SLT-VEGF/S at final concentrations from 0.078 nM to 2.5 nM. Plates were incubated for 72 hours, at 37° C., 5% $CO_2$. Following the incubation period, wells were washed with phosphate buffered saline, cells were detached with trypsin solution (Life Technologies, USA) and counted in a Coulter Counter (Coulter Corporation, USA) according to the manufacturer's instructions. SLT-VEGF/L and SLT-VEGF/S fusion proteins inhibited growth of PAE/KDR cells in a dose-dependent manner with $IC_{50}$~0.15 nM while growth of PAE/V that do not express KDR/flk-1 receptors was not affected (FIG. 5). At the low nanomolar concentration range SLT-VEGF/L proteins were cytotoxic, killing virtually all PAE/KDR cells after overnight exposure to concentration as low as 2.5 nM. In contrast, SLT-VEGF/S proteins at the low nanomolar concentrations remained mostly cytostatic with few dead cells observed at concentration 2.5 nM.

Catalytically inactive SLT-VEGF/Lci fusion protein did not affect growth of PAE/KDR and PAE/V cells (FIG. 5, Panel C) indicating that cytotoxic and cytostatic effects of SLT-VEGF/L and SLT-VEGF/S fusion proteins are due to the ribosome inactivating activity of SLT moiety.

Cytotoxic activity of SLT-VEGF/L manifested itself in rapid induction of apoptosis in PAE/KDR cells as judged by such hallmarks of apoptosis as DNA fragmentation and cleavage of α-fodrin (FIG. 6) To detect apoptotic DNA fragmentation PAE/KDR cells were plated onto 6-well plates at a density of $2\times10^5$ cells/well and exposed to 5 nM SLT-VEGF/L 24 hr later. After indicated periods of time DNA was isolated from cell lysates and fractionated on 1.5% agarose gel. To detect cleavage of 240 kDa (α-fodrin into 150 kDa and 120 kDa fragments, PAE/KDR cells were plated onto 24-well plates at a density of $4\times10^4$ cells/well and exposed to 2.5 nM SLT-VEGF/L 20 hr later for indicated periods of time. α-fodrin and its fragments were detected by Western blot analysis of the lysates of treated cells, using anti-α-fodrin antibody (Chemicon, USA).

B. Effects of VEGF-SLT/L Fusion Protein on Endothelial Cells Expressing Low Number of KDR/flk-1 Receptors and on Quiescent Endothelial Cells Endothelial cells in the normal vasculature express low number of KDR/flk-1 receptors. To minimize potential negative side effects a useful toxin-VEGF fusion protein should not be toxic for endothelial cells with low number of KDR/flk-1 receptors or to quiescent endothelial cells that constitute normal vasculature. The ability of VEGF-SLT/L fusion protein obtained above to affect endothelial cells expressing low number of KDR/flk-1 receptors was tested with human umbilical vein endothelial (HUVE) cells expressing 30,000-50,000 KDR/flk-1 receptors per cell, PAE/$KDR_{low}$ porcine aortic endothelial cells expressing ~5,000 KDR/flk-1 receptors per cell, and MS1 mouse endothelial cells expressing ~20,000 VEGFR-2/cells. HUVE, PAE/$KDR_{low}$, and MS1 cells were plated onto 24-well plates at densities of $5-10\times10^3$ cells/well and exposed to 2.5 nM SLT-VEGF/L 20 hr later. Plates were incubated for 72 hours, at 37° C., 5% $CO_2$. Following the incubation period, wells were washed with phosphate buffered saline (PBS), cells were detached with trypsin solution (Life Technologies, USA) and counted in a Coulter Counter (Coulter Corporation, USA) according to the manufacturer's instructions. SLT-VEGF/L fusion protein did not affect growing human HUVE, mouse MS1, and porcine PAE/$KDR_{low}$ endothelial cells indicating that only a high level of KDR/flk-1 receptor expression may confer sensitivity to SLT-VEGF/L fusion protein on endothelial cells (FIG. 7, panel A).

The ability of VEGF-SLT/L fusion protein obtained above to affect quiescent endothelial cells was tested with quiescent PAE/KDR cells. About 5,000 PAE/KDR cells per well were plated onto 24-well plates in 1 ml DMEM (Life Technologies, USA) supplemented with 10% fetal calf serum (Gemini, USA) and incubated at 37° C., 5% $CO_2$. Cells reached confluence after approximately one week and were maintained as quiescent for additional three days. After that the media was changed to fresh DMEM supplemented with 10% fetal calf serum, and SLT-VEGF/L at a final concentration of 20 nM. Plates were incubated for 72 hours, at 37° C., 5% $CO_2$. For comparison, growing PAE/KDR were exposed to 20 nM SLT-VEGF/L for 5 min; then shifted to fresh culture medium and counted after 72 hrs. SLT-VEGF/L proteins did not affect quiescent PAE/KDR endothelial cells even after 72-hour exposure, while dramatically affected growing PAE/KDR even after a 5-min exposure.

While the invention has been described in combination with embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims. All patent applications, patents, and other publications cited herein are incorporated by reference in their entireties.

REFERENCES

Aiello, L. P., Northrup, J. M., Keyt, B. A., Takagi, H., and Iwamoto, M. A. (1995) Hypoxic regulation of vascular endothelial growth factor in retinal cells. Arch. Opthalmol., 113, 1538-1544.

Al-Jaufy, A. Y., Haddad, J. E., King, S. R., McPhee, R. A., and Jackson, M. P. (1994) Cytotoxicity of a Shiga toxin A subunit-CD4 fusion protein to human immunodeficiency virus-infected cells. Infect. & Immun., 62, 956-960.

Al-Jaufy, A. Y., King, S. R., and Jackson, M. P. (1995) Purification and characterization of a Shiga toxin A subunit-CD4 fusion protein cytotoxic to human immunodeficiency virus-infected cells. Infect. & Immun., 63, 3073-3078.

Arora, N., Maood, R., Zheng, T., Cai, J., Smith, L., and Gill, P. S. (1999) Vascular endothelial growth factor chimeric toxin is highly active against endothelial cells. Cancer Res., 59, 183-188.

Asahara, T., Chen, D., Tsurumi, Y., Kearney, M., Rossow, S., Passeri, J., Symes, J. F., and Isner, J. M. (1996) Accelerated restitution of endothelial integrity and endothelium-dependent function after phVEGF165 gene transfer. Circulation, 94, 3291-3302.

Bikfalvi, A., Sauzeau, C., Moukadiri, H., Maclouf, J., Busso, N., Bryckaert, M., Plouet, J., and Tobelem, G. (1991) Interaction of vasculotropin/vascular endothelial cell growth factor with human umbilical vein endothelial cells: binding, internalization, degradation, and biological effects. J. Cell Physiol. 149, 50-59.

Brown, L. F., Berse, B., Jackman, R. W., Tognazzi, K., Guidi, A. J., Dvorak, H. F., Senger, D. R., Connolly, J. L., and Schnitt, S. J. (1995) Expression of vascular permeability factor (vascular endothelial growth factor) and its receptors in breast cancer. Hum, Pathol., 26, 86-91.

Brown, L. F., Berse, B., Jackman, R. W., Tognazzi, K., Manseau, E. J., Dvorak, H. F., and Senger, D. R. (1993) Increased expression of vascular permeability factor (vascular endothelial growth factor) and its receptors in kidney and bladder carcinomas. Am. J. Pathol., 143, 1255-1262.

Cao, C., Kurazono, H., Yamasaki, S., Kashiwagi, K., Igarashi, K., and Takeda, Y. (1994) Construction of mutant genes for a non-toxic verotoxin 2 variant (VT2vpl) of *Escherichia coli* and characterization of purified mutant toxins. Microbiol. Immunol., 38. 441-447.

Claffey, K. P., and Robinson, G. S. (1996) Regulation of VEGF/VPF expression in tumor cells: consequences for tumor and metastasis growth and metastasis. Cancer Metast. Rev., 15, 165-176.

Couffinhal, T., Kearney, M., witzenbichler, B., Chen, D., Murohara, T., Losordo, D. W., Symes, J., and Isner, J. M. (1997) Vascular endothelial growth factor/Vascular permeability factor (VEGF/VPF) in normal and artherosclerotic human arteries. Amer. J. Pathol. 150, 1673-1685.

Deresiewicz, R. L., Austin, P. R., and Hovde, C. J. (1993) The role of tyrosine-114 in the enzymatic activity of the Shiga-like toxin I A-chain. Mol. Gen. Genet. 241, 467-473.

Detmar, M., Brown, L. F., Claffey, K. P., Yeo, K. T., Kocher, O., Jackman, R. W., Berse, B., and Dvorak, H. F. (1994) Overexpression of vascular permeability factor/vascular endothelial growth factor and its receptors in psoriasis. J. Exp. Med., 180, 1141-1146.

Folkman, J. (1995) Angiogenesis in cancer, vascular, rheumatoid and other disease. Nature, Med., 1, 27-31.

Folkman, J., and Shing, Y. (1992) Angiogenesis. J. Biol. Chem. 267, 10931-10934.

Haddad, J. E., Al-Jaufy, A. Y., and Jackson, M. P. (1993) Minimum domain of the Shiga toxin A subunit required for enzymatic activity. J. Bacteriol., 175, 4970-4978.

Hanahan, D. (1997) Signaling vascular morphogenesis and maintenance. Science, 277, 48-60.

Iordanov, M. S., Pribnow, D., Magun, J. L., Dinh, T. H., Pearson, J. A., Chen, S. L., and Magun, B. E. (1997) Ribotoxic stress response: activation of the stress-activated protein kinase JNK1 by inhibitors of the peptidyl transferase reaction and by sequence-specific RNA damage to the alpha-sarcin/ricin loop in the 28S rRNA. Mol. Cell. Biol., 17, 3373-3381.

Kaplan, B. S., Cleary, T. G., and Obrig, T. G. (1990) Recent advances in understanding the pathogenesis of the hemolytic uremic syndromes. Pediatr. Nephrol. 4, 276-283.

Kim, K. J., Li, B., Winer, J., Armanini, M., Gillett, N., Phillips, H. S., and Ferrara, N. (1993) Inhibition of vascular endothelial growth factor-induced angiogenesis suppresses tumour growth in vivo. Nature (Lond.), 362, 841-844.

Millauer, B., Shawver, L. K., Plate, K. H., Risau, W., and Ulrich, A. (1994) Glioblastoma growth inhibited in vivo by a dominant-negative Flk-1 mutant. Nature (Lond.), 367, 576-579.

Neufeld, G., Cohen, T., Gengrinovitch, S., and Poltorak, Z. (1999) FASEB J., 13, 9-22.

Neufeld, G., Tessler, S., Gitay-Goren, H. Cohen, T., and Levi, B. Z. (1994) Vascular endothelial growth factor and its receptors. Prog. Growth Factor Res., 5, 89-97.

Obrig, T. G., Del Vecchio, P. J., Karmali, M. A., Petric, M., Moran, T. P., and Judge, T. K. (1987) Pathogenesis of haemolytic uraemic syndrome Lancet 2, 687.

Obrig, T., Louise, C., Lingwood, C., Boyd, B., Barley-Maloney, L., and Daniel, T., (1993) Endothelial heterogenecity in Shiga toxin receptors and responses. J. Biol. Chem., 268, 15484-15488.

Olsnes S., Reisbig R., and Eiklid K. (1981) Subunit structure of Shigella cytotoxin. J. Biol. Chem. 256, 48732-8738.

Olson T. A., Mohanraj, D., Roy, S., and Ramakrishnan, S. (1997) Targeting the tumor vasculature: inhibition of tumor and metastasis growth by a vascular endothelial growth factor-toxin conjugate. Int. J. Cancer 73, 865-870.

Plate, K. H., Breier, G., Millauer, B., Ullrich, A., and Risau, W. (1993) Up-regulation of vascular endothelial growth factor and its cognate receptors in a rat glioma model of tumor angiogenesis. Cancer Res. 53, 5822-5827.

Ramakrishnan, S., Olson, T. A., Bauch, V. L., and Mohanraj, D. (1996) Vascular endothelial growth factor-toxin conjugate specifically inhibits KDR/flk-1 positive endothelial cell proliferation in vitro and angiogenesis in vivo. Cancer Res. 56, 1324-1330.

Richardson, S. E., Karmali, M. A., Becker, L. E., and Smith, C. R. (1988) The histopathology of the hemolytic uremic syndrome associated with verocytotoxin-producing *Escherichia coli* infections. Hum. Pathol. 19, 1102-1108.

Saleh, M., Stacker, S. A., and Wilks, A. F. (1996) Inhibition of growth of C6 glioma cells in vivo by expression of antisense vascular endothelial growth factor sequence. Cancer Res., 56, 393-401.

Saxena, S. K., O'Brien, A. D., and Ackerman, E. J. (1989) Shiga toxin, Shiga-like toxin II variant, and ricin are all single-site RNA N-glycosideases of 28 S RNA when microinjected into *Xenopus oocytes*. J. Biol. Chem. 264, 596-601.

Terman, B. I., and Dougher-Vermazen, M. (1996) Biological properties of VEGF/VPF receptors. Cancer Metast. Rev. 15, 159-163.

Vallera, D. A., Panoskaltsis-Mortar, i A., and Blazar, B. R. (1997) Renal dysfunction accounts for the dose limiting toxicity of DT390anti-CD3sFv, a potential new recombinant anti-GVHD immunotoxin. Protein Eng. 10, 1071-1076.

Veikkola, T., and Alitalo, K. (1999) VEGFs, receptors and angiogenesis. Semin. Cancer Biol. 9, 211-220.

What is claimed is:

1. An isolated fusion polypeptide comprising:

(1) the A subunit of Shiga-like bacterial toxin, wherein said subunit is encoded by the nucleic acid sequence of SEQ ID NO:9; and (2) human vascular endothelial growth factor, wherein said growth factor is encoded by the nucleic acid sequence of SEQ ID NO:10;

wherein said isolated fusion polypeptide possesses ribosome inactivating activity.

2. The isolated fusion polypeptide of claim 1, wherein said isolated fusion polypeptide specifically binds vascular endothelial growth factor receptors.

3. The isolated fusion polypeptide of claim 2, wherein said isolated fusion polypeptide is internalized by a cell which expresses said receptors.

4. The isolated fusion polypeptide of claim 3, wherein said internalization occurs by endocytosis.

5. The isolated fusion polypeptide of claim 1, wherein said isolated fusion polypeptide is encoded by the nucleic acid of SEQ ID NO:11.

6. A composition for inhibiting endothelial cell growth in a patient, comprising:

(A) a fusion protein comprising the A subunit of Shiga-like bacterial toxin; and human vascular endothelial growth factor, said fusion protein possessing ribosome inactivating activity; and (B) a pharmaceutically acceptable carrier;

wherein said A subunit of said Shiga-like bacterial toxin, is encoded by the nucleic acid sequence of SEQ ID NO:9, and wherein said human vascular endothelial growth factor is encoded by the nucleic acid sequence of SEQ ID NO:11.

7. A fusion protein encoded by a nucleic acid sequence comprising SEQ ID NO:9 and SEQ ID NO:11.

8. A fusion protein encoded by a nucleic acid having the nucleic acid sequence of SEQ ID NO:11.

* * * * *

SEQUENCE LISTING

```
<160> NUMBER OF SEQ ID NOS: 13

<210> SEQ ID NO 1
<211> LENGTH: 26
<212> TYPE: DNA
<213> ORGANISM: Artificial Sequence
<220> FEATURE:
<223> OTHER INFORMATION: Synthetic Primer Sequence

<400> SEQUENCE: 1
taaggcctat ggcagaagga ggaggg                                     26

<210> SEQ ID NO 2
<211> LENGTH: 27
<212> TYPE: DNA
<213> ORGANISM: Artificial Sequence
<220> FEATURE:
<223> OTHER INFORMATION: Synthetic Primer Sequence

<400> SEQUENCE: 2
actcgagtca ccgcctcggc ttgtcac                                    27

<210> SEQ ID NO 3
<211> LENGTH: 28
<212> TYPE: DNA
<213> ORGANISM: Artificial Sequence
<220> FEATURE:
<223> OTHER INFORMATION: Synthetic Primer Sequence

<400> SEQUENCE: 3
ccgagatctg aaggaattta ccttagac                                   28

<210> SEQ ID NO 4
<211> LENGTH: 30
<212> TYPE: DNA
<213> ORGANISM: Artificial Sequence
<220> FEATURE:
<223> OTHER INFORMATION: Synthetic Primer Sequence

<400> SEQUENCE: 4
cccagatctg ctacggctta ttgttgaacg                                 30

<210> SEQ ID NO 5
<211> LENGTH: 27
<212> TYPE: DNA
<213> ORGANISM: Artificial Sequence
<220> FEATURE:
<223> OTHER INFORMATION: Synthetic Primer Sequence

<400> SEQUENCE: 5
ataggtacca ctgctaatag ttctgcg                                    27

<210> SEQ ID NO 6
<211> LENGTH: 29
<212> TYPE: DNA
<213> ORGANISM: Artificial Sequence
<220> FEATURE:
<223> OTHER INFORMATION: Synthetic Primer Sequence
```

```
<400> SEQUENCE: 6
ataggtacca tctgccggac acatagaag                                           29

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer Sequence

<400> SEQUENCE: 7
acgtggtaga gctactgtca cc                                                  22

<210> SEQ ID NO 8
<211> LENGTH: 32
<212> TYPE: DNA
<213> ORGANISM: Artificial Sequence
<220> FEATURE:
<223> OTHER INFORMATION: Synthetic Primer Sequence

<400> SEQUENCE: 8
ttgccgaaaa agtaaagctt gagctgtcac ag                                       32

<210> SEQ ID NO 9
<211> LENGTH: 879
<212> TYPE: DNA
<213> ORGANISM: Human

<400> SEQUENCE: 9
aaggaattta ccttagactt ctcgactgca aagacgtatg tagattcgct gaatgtcatt         60
cgctctgcaa taggtactcc attacagact atttcatcag gaggtacgtc tttactgatg        120
attgatagtg gcacagggga taatttgttt gcagttgatg tcagagggat agatccagag        180
gaagggcggt ttaataatct acggcttatt gttgaacgaa ataatttata tgtgacagga        240
tttgttaaca ggacaaataa tgttttttat cgctttgctg attttttcaca tgttaccttt       300 ccaggtacaa cagcggttac attgtctggt gacagtagct ataccacgtt acagcgtgtt        360
gcagggatca gtcgtacggg gatgcagata aatcgccatt cgttgactac ttcttatctg        420
gatttaatgt cgcatagtgg aacctcactg acgcagtctg tggcaagagc gatgttacgg        480
tttgttactg tgacagctga agctttacgt tttcggcaaa tacagagggg atttcgtaca        540
acactggatg atctcagtgg gcgttcttat gtaatgactg ctgaagatgt tgatcttaca        600
ttgaactggg gaaggttgag tagcgtcctg cctgactatc atggacaaga ctctgttcgt        660
gtaggaagaa tttctttttgg aagcattaat gcaattctgg gaagcgtggc attaatactg       720
aattgtcatc atcatgcatc gcgagttgcc agaatggcat ctgatgagtt ccttctatg        780 tgtccggcag atggaagagt ccgtgggatt acgcacaata aaatattgtg ggattcatcc        840
actctggggg caattctgat gcgcagaact attagcagt                               879

<210> SEQ ID NO 10
<211> LENGTH: 498
<212> TYPE: DNA
<213> ORGANISM: Human

<400> SEQUENCE: 10
gcacccatgg cagaaggagg agggcagaat catcacgaag tggtgaagtt catggatgtc         60
tatcagcgca gctactgcca tccaatcgag accctggtgg acatcttcca ggagtaccct        120
gatgagatcg agtacatctt caagccatcc tgtgtgcccc tgatgcgatg cggggggctgc       180
```

```
tgcaatgacg agggcctgga gtgtgtgccc actgaggagt ccaacatcac catgcagatt      240
atgcggatca aacctcacca aggccagcac ataggagaga tgagcttcct acagcacaac      300
aaatgtgaat gcagaccaaa gaaagataga gcaagacaag aaaatccctg tgggccttgc      360
tcagagcgga gaaagcattt gtttgtacaa gatccgcaga cgtgtaaatg ttcctgcaaa      420
aacacagact cgcgttgcaa ggcgaggcag cttgagttaa cgaacgtac ttgcagatgt       480 gacaagccga ggcggtga                                                    498

<210> SEQ ID NO 11
<211> LENGTH: 1507
<212> TYPE: DNA
<213> ORGANISM: Artificial Sequence
<220> FEATURE:
<223> OTHER INFORMATION: Synthetic Construct

<400> SEQUENCE: 11
atgcaccatc atcatcatca ttcttctggt ctggtgccac gcggttctgg tatgaaagaa       60
accgctgctg ctaaattcga acgccagcac atggacagcc cagatctgaa ggaatttacc      120
ttagacttct cgactgcaaa gacgtatgta gattcgctga atgtcattcg ctctgcaata      180
ggtactccat tacagactat ttcatcagga ggtacgtctt tactgatgat tgatagtggc      240
acaggggata atttgtttgc agttgatgtc agagggatag atccagagga agggcggttt      300
aataatctac ggcttattgt tgaacgaaat aatttatatg tgacaggatt tgttaacagg      360
acaaataatg ttttttatcg ctttgctgat ttttcacatg ttacctttcc aggtacaaca      420
gcggttacat tgtctggtga cagtagctat accacgttac agcgtgttgc agggatcagt      480
cgtacgggga tgcagataaa tcgccattcg ttgactactt cttatctgga tttaatgtcg      540
catagtggaa cctcactgac gcagtctgtg gcaagagcga tgttacggtt tgttactgtg      600
acagctgaag ctttacgttt tcggcaaata cagagggggt tcgtacaac actggatgat       660 ctcagtgggc gttcttatgt aatgactgct gaagatgttg atcttacatt gaactgggga      720
aggttgagta gcgtcctgcc tgactatcat ggacaagact ctgttcgtgt aggaagaatt      780
tcttttggaa gcattaatgc aattctggga agcgtggcat taatactgaa ttgtcatcat      840
catgcatcgc gagttgccag aatggcatct gatgagtttc cttctatgtg tccggcagat      900
ggaagagtcc gtgggattac gcacaataaa atattgtggg attcatccac tctgggggca      960
attctgatgc gcagaactat tagcagtggg taccgacgac gacgcacaagg cacccatggc    1020 agaaggagga gggcagaatc atcacgaagt ggtgaagttc atggatgtct atcagcgcag     1080
ctactgccat ccaatcgaga ccctggtgga catcttccag gagtaccctg atgagatcga     1140
gtacatcttc aagccatcct gtgtgccct gatgcgatgc ggggctgct gcaatgacga      1200 gggcctggag tgtgtgccca ctgaggagtc caacatcacc atgcagatta tgcggatcaa     1260
acctcaccaa ggccagcaca taggagagat gagcttccta cagcacaaca atgtgaatg     1320 cagaccaaag aaagatagag caagacaaga aaatccctgt gggccttgct cagagcggag    1380
aaagcatttg tttgtacaag atccgcagac gtgtaaatgt tcctgcaaaa acacagactc    1440
gcgttgcaag gcgaggcagc ttgagttaaa cgaacgtact tgcagatgtg acaagccgag    1500
gcggtga                                                               1507

<210> SEQ ID NO 12
<211> LENGTH: 107
<212> TYPE: DNA
```

-continued

```
<213> ORGANISM: Artificial Sequence
<220> FEATURE:
<223> OTHER INFORMATION: Synthetic Construct

<400> SEQUENCE: 12
atgcaccatc atcatcatca ttcttctggt ctggtgccac gcggttctgg tatgaaagaa     60
accgctgctg ctaaattcga acgccagcac atggacagcc cagatct                  107

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

<400> SEQUENCE: 13
gggtaccgac gacgacgaca ag                                              22
```